United States Patent
Hammock et al.

(10) Patent No.: US 9,034,903 B2
(45) Date of Patent: May 19, 2015

(54) ACYL PIPERIDINE INHIBITORS OF SOLUBLE EPOXIDE HYDROLASE

(71) Applicant: The Regents of the University of California, Oakland, CA (US)

(72) Inventors: Bruce D. Hammock, Davis, CA (US); Kin Sing Lee, Davis, CA (US); Christophe Morisseau, West Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/375,224

(22) PCT Filed: Feb. 1, 2013

(86) PCT No.: PCT/US2013/024396
§ 371 (c)(1),
(2) Date: Jul. 29, 2014

(87) PCT Pub. No.: WO2013/116690
PCT Pub. Date: Aug. 8, 2013

(65) Prior Publication Data
US 2015/0011586 A1    Jan. 8, 2015

Related U.S. Application Data

(60) Provisional application No. 61/593,805, filed on Feb. 1, 2012.

(51) Int. Cl.
 C07D 211/58  (2006.01)
 C12N 9/14   (2006.01)
 C12Q 1/34   (2006.01)

(52) U.S. Cl.
 CPC ............. *C07D 211/58* (2013.01); *C12N 9/14* (2013.01); *C12Q 1/34* (2013.01); *C12Y 303/0201* (2013.01)

(58) Field of Classification Search
 CPC .. C12N 9/14; C07D 211/58; C12Y 303/0201; C12Q 1/34
 USPC ............. 514/329; 435/18, 184; 546/244
 See application file for complete search history.

(56) References Cited

U.S. PATENT DOCUMENTS

| | | |
|---|---|---|
| 8,476,043 B2 | 7/2013 | Hammock et al. |
| 2008/0227780 A1 | 9/2008 | Gless et al. |
| 2009/0247521 A1 | 10/2009 | Aavula et al. |
| 2009/0270452 A1 | 10/2009 | Webb Hsu et al. |
| 2010/0063583 A1 | 3/2010 | Wang et al. |
| 2011/0021448 A1 | 1/2011 | Hammock et al. |

*Primary Examiner* — John Mabry
(74) *Attorney, Agent, or Firm* — DLA Piper LLP (US)

(57) ABSTRACT

Inhibitors of the soluble epoxide hydrolase (sEH) are provided that incorporate multiple pharmacophores and are useful in the treatment of diseases. In some embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said sEH.

9 Claims, 8 Drawing Sheets

Figure 1
Synthetic Method 1
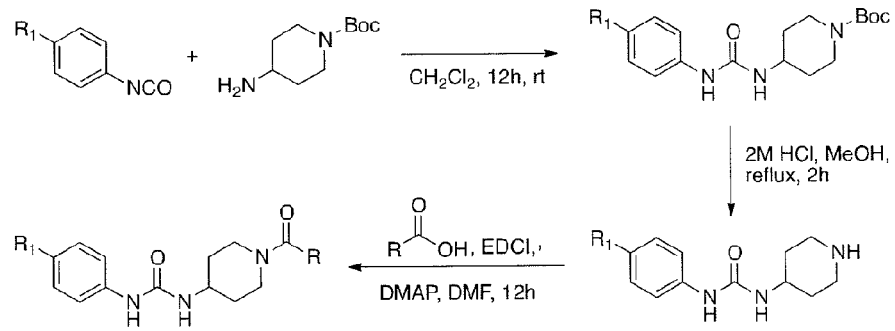
Synthetic Method 2
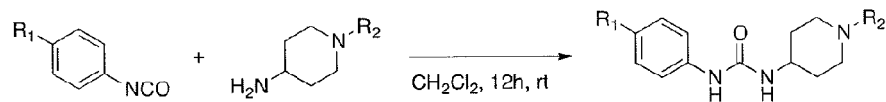
Synthetic Method 3
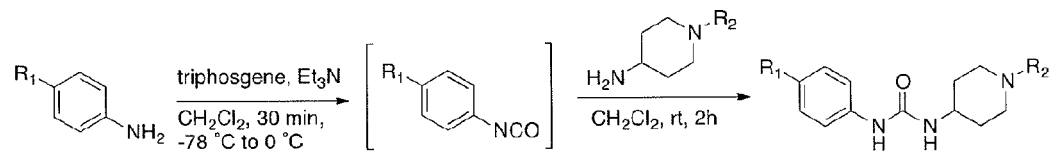
Synthetic Method 4
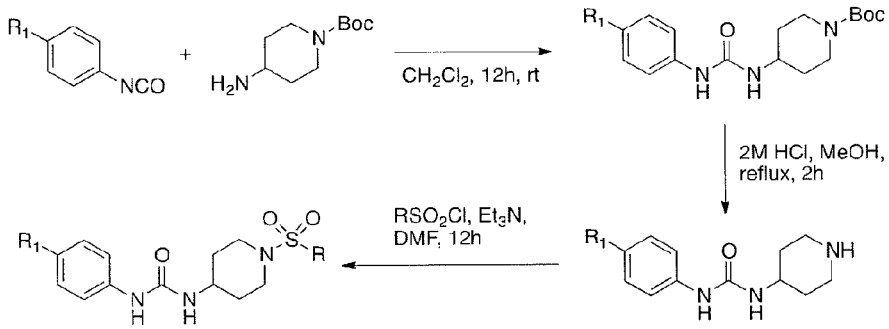

| Structure | Physical Properties ||| Human || Mouse |||| Rat ||||
|---|---|---|---|---|---|---|---|---|---|---|---|---|---|
| | Mol. Wt. | Sol$^c$ (ug/mL) | Melting Point (°C) | Ki (nM) (sEH) | $k_{off}$/$t_{1/2}$ (x10$^{-4}$ s$^{-1}$/min) (sEH)$^d$ | Ki (nM) (sEH) | $k_{off}$/$t_{1/2}$ (x10$^{-4}$ s$^{-1}$/min) (sEH)$^d$ | AUC$^b$ (nM*h)/C$_{max}$ (nM) @0.3 mpk | T$_{1/2}^b$/T$_{max}$(h) @0.3 mpk | IC$_{50}$ (nM) (sEH) | $k_{off}$/$t_{1/2}$ (x10$^{-4}$ s$^{-1}$/min) (sEH)$^d$ | AUC$^e$ (nM*h)/C$_{max}$ (nM) @0.3 mpk | T$_{1/2}^e$/T$_{max}$(h) @0.3 mpk |
|  1153 | 319.44 | 277 | 205-206 (205.5) | 21.7 | 19.1/6 | 1.86 | 3.7/31 | 183/30 @0.5 mpk | 3/1 | 2.9 | 2.9/40 | | |
|  1770 | 359.34 | 60 | 198.2-200.8 (199.5) | 0.64 ±0.09 | 10.9/11 | 6.22 | 5.8/20 | 10650 (495) | 12.1 (8) | 33.1 | 9.1/13 | 11814.7 ±2314 | 10.64 ±2.23 |
|  2389 | 357.37 | 7.2 | 234.1-235.4 (234.9) | 0.66 | 6.6/18 | 9.35 | 6.0/19 | 19650 (1160) | 6 (4) | 1.7 | 3.3/35 | 7303.6 ±2750.2 | 5.38 ±0.48 |
|  2422 | 373.37 | 27 | 179.1-180.3 (179.6) | 0.31 ±0.18 | 6.1/19 | 5.11 | 4.8/24 | 19500 (900) | 9 (5) | 12.2 | 6.9/17 | 12000.8 ±3439.4 | 3.48 ±0.21 |
|  2391 | 371.40 | 9.2 | 221.3-225.6 (221.6) | 0.19 | 5.2/22 | 5.49 | 5.1/22 | 4940 (435) | 5 (1) | <1 | 4.3/27 | 5716.3 ±2348.9 | 4.86 ±1.33 |
|  2696 | 387.40 | 21.3 | 168.0-169.3 (168.7) | 0.22 | 5.1/23 | 2.30 | 4.4/26 | 2530 (195) | 7.7 (4) | 20 | 4.8/24 | 2590.3 ±822.4 | 4.24 ±0.25 |
|  2383 | 371.40 | 2.6 | 225.2-226.3 (225.9) | 0.38 ±0.04 | 5.8/20 | | | 3295 (320) | 6 (0.5) | 1.7 | | | |
|  2385 | 387.40 | 22.5 | 170.9-171.6 (171.3) | 0.36 ±0.09 | 5.4/21 | | | 3300 (235) | 6 (2) | 10.5 | | | |
|  2415 | 355.35 | 19.7 | 193.4-194.2 (193.7) | 0.87 | 7.9/15 | 8.68 | 5.7/20 | 24630 (960) | 17 (6) | 1.4 | 3.8/30 | | |
|  2214 | 371.35 | 4.6 | 193.4-194.2 (193.8) | 0.57 | 6.6/18 | 3.3 | 4.9/24 | | | <1.2 | 7.1/16 | | |
|  2602 | 385.42 | 1.5 | 207.9-209.3 (208.6) | 0.06 ±0.01 | 4.2/28 | | | 430 (60) | 5.5 (2) | | | | |
|  2601 | 401.42 | 3.4 | 167.0-167.4 (167.2) | 0.05 ±0.01 | 4.4/27 | | | 2090 (205) | 3.5 (1.3) | | | | |
|  2551 | 345.48 | 2.6 | 174.0-174.9 (174.5) | 1.1 | 5.8/20 | | | 200 (90) | 2 (0.5) | | | | |

FIG. 2A

| | Physical Properties | | | Human | | Mouse | | | | Rat | | |
|---|---|---|---|---|---|---|---|---|---|---|---|---|
| 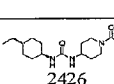 2426 | 323.47 | 71.6 | 186.0-188.4 (186.8) | 0.19 | 3.6 / 32 | | | 100 (30) | 2 (1.8) | | | |
| 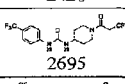 2695 | 397.32 | 3.23 | 209.2-210.7 (210.3) | 0.22 | 4.8 / 24 | | | 4270 (100) | 25 (8) | | | |
| 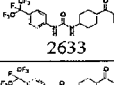 2633 | 471.42 | 0.17 | 182.2-183.2 (182.8) | 0.04 | 3.4 / 34 | | | 1600 (135) | 4.5 (2.5) | | | |
| 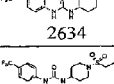 2634 | 496.34 | 12.3 | | <0.02 | 3.1 / 37 | 0.89 | 3.3 / 35 | 9600 (365) | 18.9 (8) | 6.2 | 3.8 / 30 | |
| 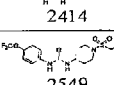 2414 | 407.45 | 0.08 | >220 (decompose) | 0.98 | 10.3 / 11 | 1.08 | 4.2 / 28 | 245 (30) | 7.4 (1) | 1.9 | 3.6 / 32 | |
| 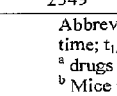 2549 | 423.14 | 0.6 | >220 (decompose) | 0.34 | 8.9 / 13 | 0.70 | 2.9 / 40 | 220 (65) | 2 (1.2) | 3.6 | 5.0 / 23 | |

Abbreviation: Sol: solubility; $K_i$: inhibition constant; $AUC_t$: area under the concentration–time curve to terminal time; $t_{1/2a}$: first order absorption half life, $t_{1/2d}$: first order apparent half life.
[a] drugs were formulated with 10% (v/v) PEG400 in oleic acid-rich triglyceride in OO Capsule.
[b] Mice were treated by oral gavage which drugs were formulated with 20% (v/v) PEG400 in oleic acid-rich triglyceride. The results were an average of 8 mice.
[c] The solubility of the drugs were measured at Phosphate Buffer at pH 7.4
[d] $t_{1/2}$ defined as the time required for half of the drug being dissociated from the enzyme based on the fluorescence signals.
[e] Rats were treated by oral gavage which drugs were formulated with 20% (v/v) PEG400 in oleic acid-rich triglyceride. The results were an average of 8 mice.

FIG. 2B

Figure 6
Rodent PK (Cassette Dose)
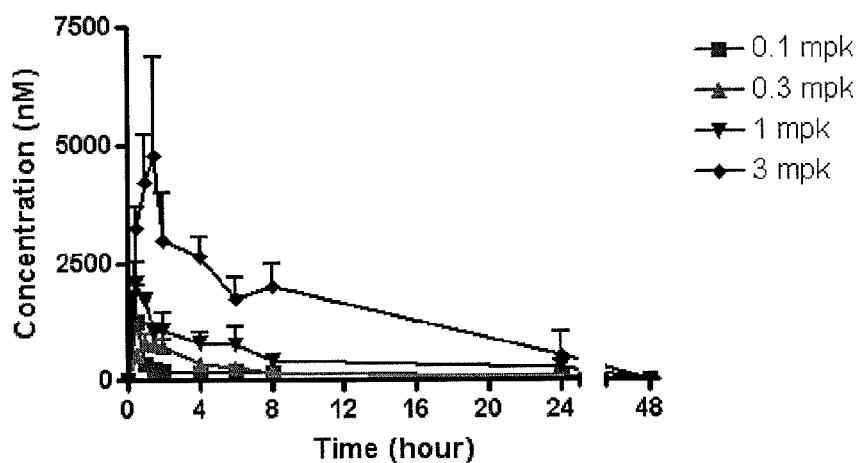
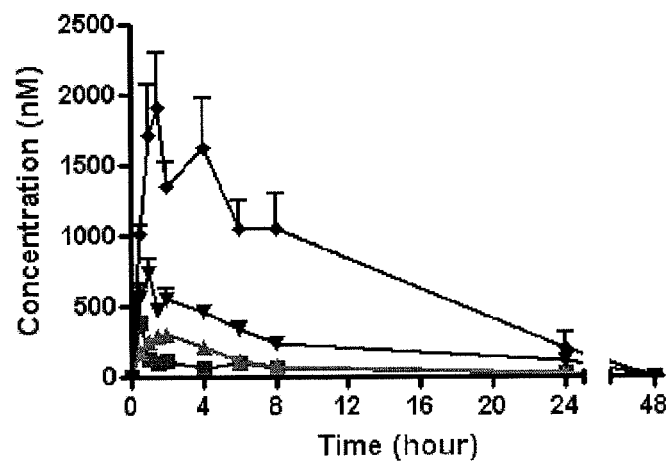

Rodent PK (Cassette Dose)

ACYL PIPERIDINE INHIBITORS OF SOLUBLE EPOXIDE HYDROLASE

CROSS-REFERENCES TO RELATED APPLICATIONS

This application is a 35 USC §371 National Stage application of International Application No. PCT/US2013/024396 filed Feb. 1, 2013, now pending; which claims the benefit under 35 USC §119(e) to U.S. Application Ser. No. 61/593,805 filed Feb. 1, 2012. The disclosure of each of the prior applications is considered part of and is incorporated by reference in the disclosure of this application.

STATEMENT AS TO RIGHTS TO INVENTIONS MADE UNDER FEDERALLY SPONSORED RESEARCH AND DEVELOPMENT

This invention was made with government support under Grant No. ES002710 awarded by the National Institute of Environmental Health Sciences. The government has certain rights in the invention.

BACKGROUND OF THE INVENTION

Epoxide hydrolases (EHs, EC 3.3.2.3) catalyze the hydrolysis of epoxides or arene oxides to their corresponding diols by the addition of water (see, Oesch, F., et al., *Xenobiotica* 1973, 3, 305-340). Some EHs play an important role in the metabolism of a variety of compounds including hormones, chemotherapeutic drugs, carcinogens, environmental pollutants, mycotoxins, and other harmful foreign compounds.

There are two well-studied EHs, microsomal epoxide hydrolase (mEH) and soluble epoxide hydrolase (sEH). These enzymes are very distantly related, have different subcellular localization, and have different but partially overlapping substrate selectivities. The soluble and microsomal EH forms are known to complement each other in degrading some plant natural products (see, Hammock, B. D., et al., COMPREHENSIVE TOXICOLOGY. Oxford: Pergamon Press 1977, 283-305 and Fretland, A. J., et al., *Chem. Biol. Intereract* 2000, 129, 41-59).

The major role of the sEH is in the metabolism of lipid epoxides including the metabolism of arachidonic acid (see, Zeldin, D. C., et al., *J. Biol. Chem.* 1993, 268, 6402-6407), linoleic acid (see, Moghaddam, M. F., et al., *Nat. Med.* 1997, 3, 562-567) acid, some of which are endogenous chemical mediators (see, Carroll, M. A., et al., *Thorax* 2000, 55, S13-16). Epoxides of arachidonic acid (epoxyeicosatrienoic acids or EETs) and other lipid epoxides and diols are known effectors of blood pressure (see, Capdevila, J. H., et al., *J. Lipid. Res.* 2000, 41, 163-181), and modulators of vascular permeability (see, Oltman, C. L., et al., *Circ Res.* 1998, 83, 932-939). The vasodilatory properties of EETs are associated with an increased open-state probability of calcium-activated potassium channels leading to hyperpolarization of the vascular smooth muscle (see Fisslthaler, B., et al., *Nature* 1999, 401, 493-497). Hydrolysis of the arachidonate epoxides by sEH diminishes this activity (see, Capdevila, J. H., et al., *J. Lipid. Res.* 2000, 41, 163-181). sEH hydrolysis of EETs also regulates their incorporation into coronary endothelial phospholipids, suggesting a regulation of endothelial function by sEH (see, Weintraub, N. L., et al., *Am. J. Physiol.* 1992, 277, H2098-2108). It has recently been shown that treatment of spontaneous hypertensive rats (SHRs) with selective sEH inhibitors significantly reduces their blood pressure (see, Yu, Z., et al., *Circ. Res.* 2000, 87, 992-998). In addition, it was claimed that male knockout sEH mice have significantly lower blood pressure than wild-type mice (see Sinal, C. J., et al., *J. Biol. Chem.* 2000, 275, 40504-405010), however subsequent studies demonstrated with back breeding into C57b mice that 20-HETE levels increased compensating for the increase in plasma EETs (see, Luria, A. et al., *J. Biol. Chem.* 2007, 282:2891-2898.

The EETs have also demonstrated anti-inflammatory properties in endothelial cells (see, Node, K., et al., *Science* 1999, 285, 1276-1279 and Campbell, W. B. *Trends Pharmacol. Sci.* 2000, 21, 125-127). In contrast, diols derived from epoxylinoleate (leukotoxin) perturb membrane permeability and calcium homeostasis (see, Moghaddam, M. F., et al., *Nat. Med.* 1997, 3, 562-567), which results in inflammation that is modulated by nitric oxide synthase and endothelin-1 (see, Ishizaki, T., et al., *Am. J. Physiol.* 1995, 269, L65-70 and Ishizaki, T., et al., *J. Appl. Physiol.* 1995, 79, 1106-1611). Micromolar concentrations of leukotoxin reported in association with inflammation and hypoxia (see, Dudda, A., et al., *Chem. Phys. Lipids* 1996, 82, 39-51), depress mitochondrial respiration in vitro (see, Sakai, T., et al., *Am. J. Physiol.* 1995, 269, L326-331), and cause mammalian cardiopulmonary toxicity in vivo (see, Ishizaki, T., et al., *Am. J. Physiol.* 1995, 269, L65-70; Fukushima, A., et al., *Cardiovasc. Res.* 1988, 22, 213-218; and Ishizaki, T., et al., *Am. J. Physiol.* 1995, 268, L123-128). Leukotoxin toxicity presents symptoms suggestive of multiple organ failure and acute respiratory distress syndrome (ARDS) (see, Ozawa, T. et al., *Am. Rev. Respir. Dis.* 1988, 137, 535-540). In both cellular and organismal models, leukotoxin-mediated toxicity is dependent upon epoxide hydrolysis (see, Moghaddam, M. F., et al., *Nat. Med.* 1997, 3, 562-567; Morisseau, C., et al., *Proc. Natl. Acad. Sci. USA* 1999, 96, 8849-8854; and Zheng, J., et al., *Am. J. Respir. Cell Mol. Biol.* 2001, 25, 434-438), suggesting a role for sEH in the regulation of inflammation and vascular permeability. The bioactivity of these epoxy-fatty acids suggests that inhibition of vicinal-dihydroxy-lipid biosynthesis may have therapeutic value, making sEH a promising pharmacological target.

Recently, 1,3-disubstituted ureas, carbamates, and amides have been reported as new potent and stable inhibitors of sEH See, U.S. Pat. No. 6,150,415. Compounds 192 and 686 are representative structures for this type of inhibitors (FIG. 1, therein). These compounds are competitive tight-binding inhibitors with nanomolar $K_I$ values that interact stoichiometrically with purified recombinant sEH (see, Morisseau, C., et al., *Proc. Natl. Acad. Sci. USA* 1999, 96, 8849-8854). Based on the X-ray crystal structure, the urea inhibitors were shown to establish hydrogen bonds and to form salt bridges between the urea function of the inhibitor and residues of the sEH active site, mimicking features encountered in the reaction coordinate of epoxide ring opening by this enzyme (see, Argiriadi, M. A., et al., *Proc. Natl. Acad. Sci. USA* 1999, 96, 10637-10642 and Argiriadi, M. A., et al., *J. Biol. Chem.* 2000, 275, 15265-15270). These inhibitors efficiently reduced epoxide hydrolysis in several in vitro and in vivo models (see, Yu, Z., et al., *Circ. Res.* 2000, 87, 992-998; Morisseau, C., et al., *Proc. Natl. Acad. Sci. USA* 1999, 96, 8849-8854; and Newman, J. W., et al., *Environ. Health Perspect.* 2001, 109, 61-66). Despite the high activity associated with these inhibitors, there exists a need for compounds possessing similar or increased activities, preferably with improved solubility and/or pharmacokinetic properties to facilitate formulation and delivery.

The present invention provides such compounds along with methods for their use and compositions that contain them.

BRIEF SUMMARY OF THE INVENTION

In some embodiments, the present invention provides a compound of 1-(1-(2-methylbutyryl)piperidin-4-yl)-3-(4-(trifluoromethoxy)phenyl)urea, (S)-1-(1-(2-methylbutanoyl) piperidin-4-yl)-3-(4-(trifluoromethyl)phenyl)urea, 1-(1-isobutyrylpiperidin-4-yl)-3-(4-(trifluoromethoxy)phenyl) urea, 1-(1-(2-ethylbutanoyl)piperidin-4-yl)-3-(4-(trifluoromethoxy)phenyl)urea, 1-(1-(2-ethylbutanoyl) piperidin-4-yl)-3-(4-(trifluoromethyl)phenyl)urea, (S)-1-(1-(2-methylbutanoyl)piperidin-4-yl)-3-(4-(trifluoromethoxy) phenyl)urea, 1-cyclohexyl-3-(1-(2-methylbutanoyl) piperidin-4-yl)urea, 1-cycloheptyl-3-(1-(2-methylbutanoyl) piperidin-4-yl)urea, 1-(4-isopropylphenyl)-3-(1-(2-methylbutanoyl)piperidin-4-yl)urea, 1-(3,5-di-trifluoromethylphenyl)-3-(1-(2-methylbutanoyl)piperidin-4-yl)urea, 1-(4-tert-butylphenyl)-3-(1-(2-methylbutanoyl) piperidin-4-yl)urea, 1-(4-ethylcyclohexyl)-3-(1-isobutyrylpiperidin-4-yl)urea, or salts and isomers thereof.

In another embodiment, the present invention provides a pharmaceutical composition, including a compound of the present invention and a pharmaceutically acceptable excipient.

In view of the above, the present invention provides, in one aspect, a method for inhibiting a soluble epoxide hydrolase, comprising contacting the soluble epoxide hydrolase with an inhibiting amount of a compound of the present invention.

In other embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said sEH.

BRIEF DESCRIPTION OF THE DRAWINGS

FIG. 1 shows synthetic schemes 1-4 for preparation of the compounds of the present invention.

FIGS. 2A-2B show a table of activity data for the compounds of the present invention, and prior art compounds.

FIG. 6 shows blood concentration levels for compounds 2391 and 2696 at various administration doses in rats at 0.1, 0.3, 1 and 3 MPK. Rats were treated by oral gavage which drugs were formulated with 20% (v/v) PEG400 in oleic acid-rich triglyceride. The results were an average of 8 rats.

DETAILED DESCRIPTION OF THE INVENTION

I. Abbreviations and Definitions

Figure 3:
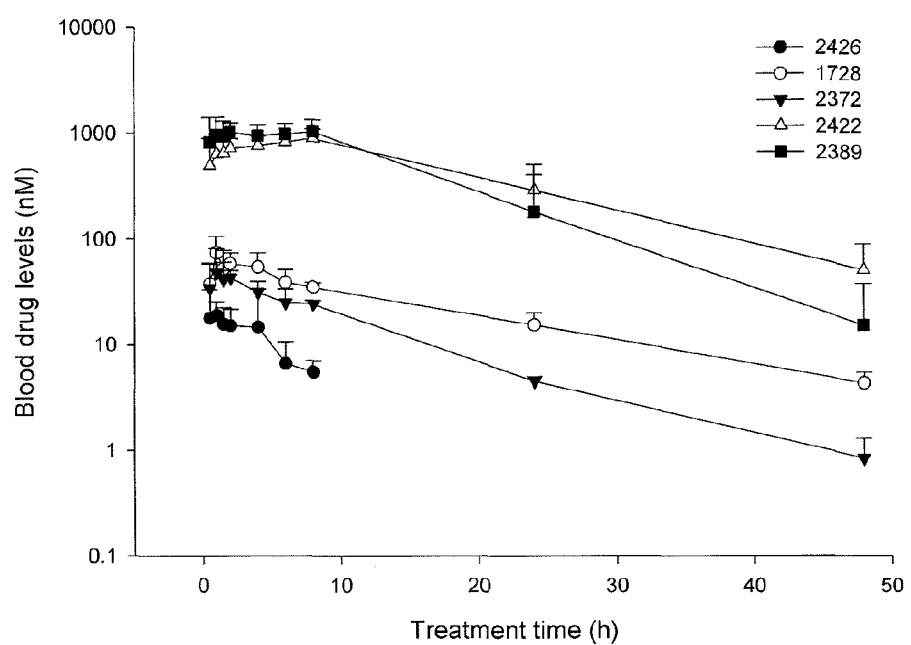
FIG. 3 shows blood drug levels for compounds 1728, 2372, 2389, 2422 and 2426 in mice administered at 0.3 mg/kg (MPK). Mice were treated by oral gavage which drugs were formulated with 20% (v/v) PEG400 in oleic acid-rich triglyceride. The results were an average of 8 mice.
Figure 4:
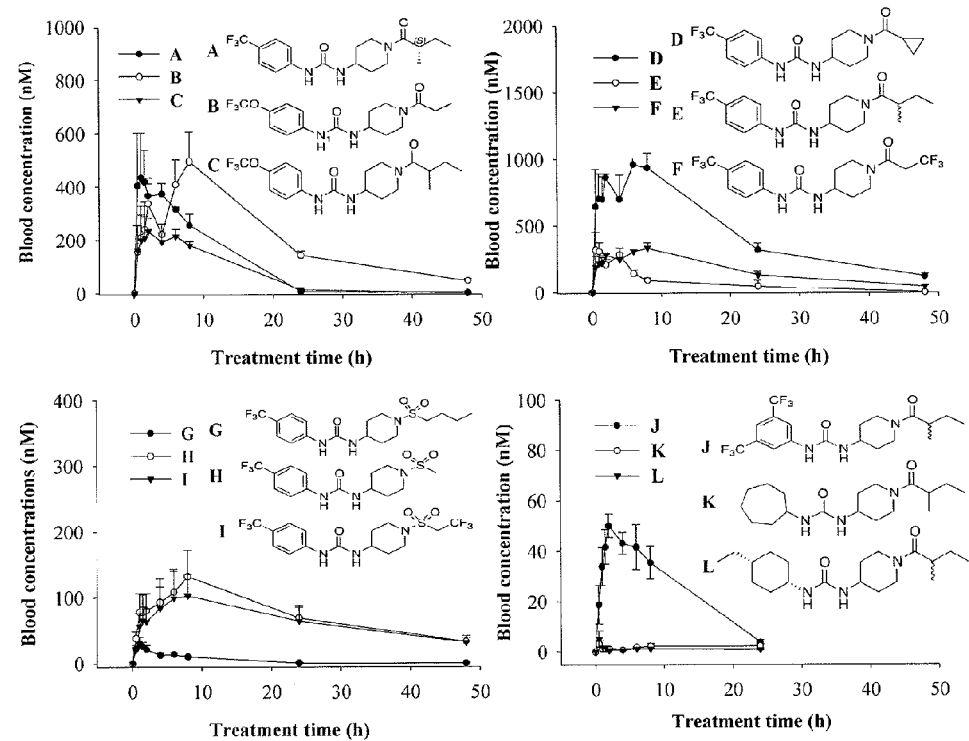
FIG. 4 shows blood concentration levels in mice for a variety of compounds of the present invention where the compounds were administered at 0.3 mg/kg (MPK). Mice were treated by oral gavage which drugs were formulated with 20% (v/v) PEG400 in oleic acid-rich triglyceride. The results were an average of 8 mice.
Figure 5:
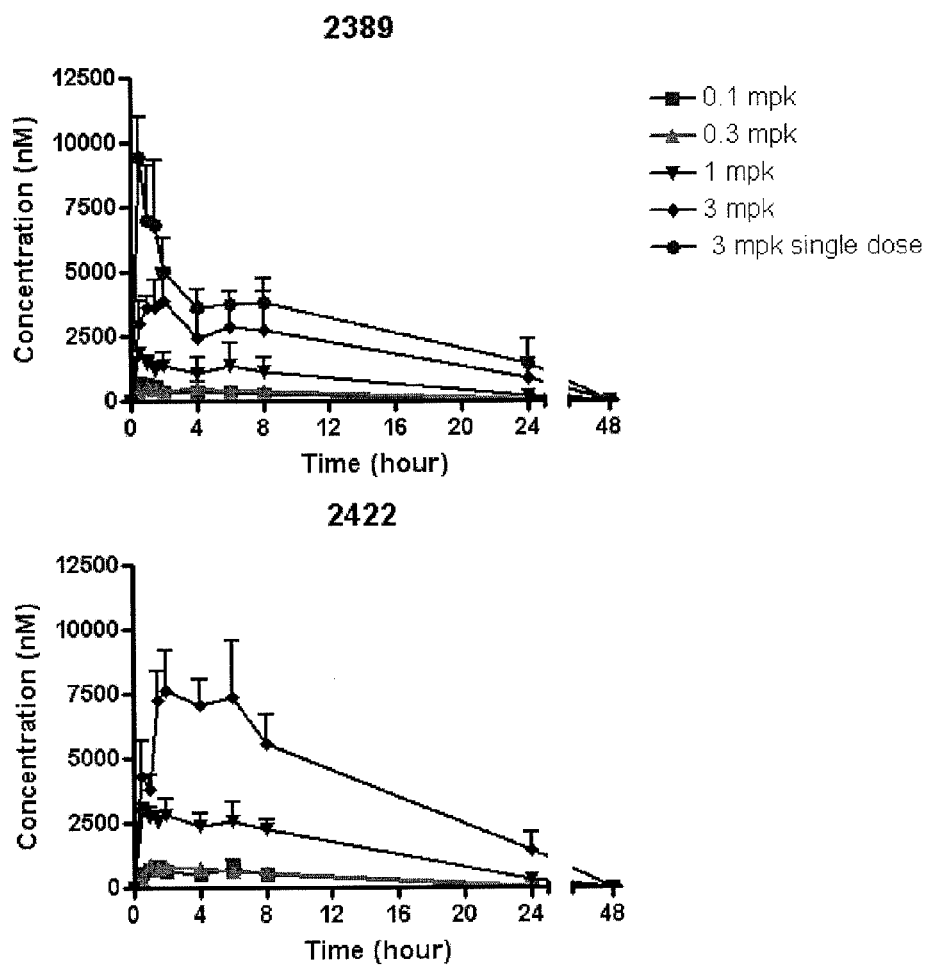
FIG. 5 shows blood concentration levels for compounds 2389 and 2422 at various administration doses in rats at 0.1, 0.3, 1 and 3 MPK, plus another rat at a single dose of 3 MPK. Rats were treated by oral gavage which drugs were formulated with 20% (v/v) PEG400 in oleic acid-rich triglyceride. The results were an average of 8 rats.
Figure 7:
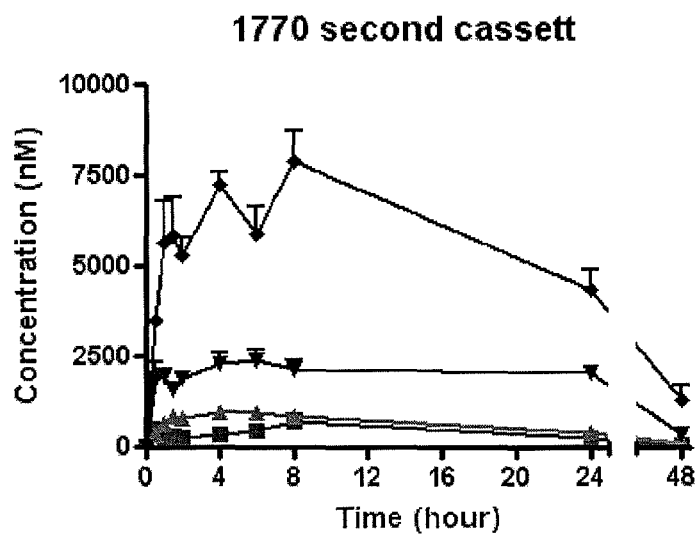
FIG. 7 shows blood concentration levels for compound 1770 at various administration doses in rats at 0.1, 0.3, 1 and 3 MPK. Rats were treated by oral gavage which drugs were formulated with 20% (v/v) PEG400 in oleic acid-rich triglyceride. The results were an average of 8 rats.

"cis-Epoxyeicosatrienoic acids" ("EETs") are biomediators synthesized by cytochrome P450 epoxygenases.

"Epoxide hydrolases" ("EH;" EC 3.3.2.3) are enzymes in the alpha/beta hydrolase fold family that add water to 3 membered cyclic ethers termed epoxides.

"Soluble epoxide hydrolase" ("sEH") is an enzyme which in endothelial, smooth muscle and other cell types converts EETs to dihydroxy derivatives called dihydroxyeicosatrienoic acids ("DHETs"). The cloning and sequence of the murine sEH is set forth in Grant et al., *J. Biol. Chem.* 268(23): 17628-17633 (1993). The cloning, sequence, and accession numbers of the human sEH sequence are set forth in Beetham et al., *Arch. Biochem. Biophys.* 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., *DNA Cell Biol.* 14(1):61-71 (1995). Soluble epoxide hydrolase represents a single highly conserved gene product with over 90% homology between rodent and human (Arand et al., *FEBS Lett.*, 338:251-256 (1994)).

The terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

The term "modulate" refers to the ability of a compound to increase or decrease the function, or activity, of the associated activity (e.g., soluble epoxide hydrolase). "Modulation", as used herein in its various forms, is meant to include antagonism and partial antagonism of the activity associated with sEH. Inhibitors of sEH are compounds that, e.g., bind to, partially or totally block the enzyme's activity.

The term "compound" as used herein is intended to encompass not only the specified molecular entity but also its pharmaceutically acceptable, pharmacologically active derivatives, including, but not limited to, salts, prodrug conjugates such as esters and amides, metabolites, hydrates, solvates and the like.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The term "subject" is defined herein to include animals such as mammals, including, but not limited to, primates (e.g., humans), cows, sheep, goats, horses, dogs, cats, rabbits, rats, mice and the like. In some embodiments, the subject is a human.

The term "sEH-mediated disease or condition" and the like refers to a disease or condition characterized by less than or greater than normal, sEH activity. A sEH-mediated disease or condition is one in which modulation of sEH results in some effect on the underlying condition or disease (e.g., a sEH inhibitor or antagonist results in some improvement in patient well-being in at least some patients).

"Parenchyma" refers to the tissue characteristic of an organ, as distinguished from associated connective or supporting tissues.

"Chronic Obstructive Pulmonary Disease" or "COPD" is also sometimes known as "chronic obstructive airway disease", "chronic obstructive lung disease", and "chronic airways disease." COPD is generally defined as a disorder characterized by reduced maximal expiratory flow and slow forced emptying of the lungs. COPD is considered to encompass two related conditions, emphysema and chronic bronchitis. COPD can be diagnosed by the general practitioner using art recognized techniques, such as the patient's forced vital capacity ("FVC"), the maximum volume of air that can be forcibly expelled after a maximal inhalation. In the offices of general practitioners, the FVC is typically approximated by a 6 second maximal exhalation through a spirometer. The definition, diagnosis and treatment of COPD, emphysema, and chronic bronchitis are well known in the art and discussed in detail by, for example, Honig and Ingram, in Harrison's Principles of Internal Medicine, (Fauci et al., Eds.), 14th Ed., 1998, McGraw-Hill, New York, pp. 1451-1460 (hereafter, "Harrison's Principles of Internal Medicine").

"Emphysema" is a disease of the lungs characterized by permanent destructive enlargement of the airspaces distal to the terminal bronchioles without obvious fibrosis.

"Chronic bronchitis" is a disease of the lungs characterized by chronic bronchial secretions which last for most days of a month, for three months a year, for two years.

As the names imply, "obstructive pulmonary disease" and "obstructive lung disease" refer to obstructive diseases, as opposed to restrictive diseases. These diseases particularly include COPD, bronchial asthma and small airway disease.

"Small airway disease" refers to the minority of patients whose airflow obstruction is due, solely or predominantly to involvement of the small airways. These are defined as airways less than 2 mm in diameter and correspond to small cartilaginous bronchi, terminal bronchioles and respiratory bronchioles. Small airway disease (SAD) represents luminal obstruction by inflammatory and fibrotic changes that increase airway resistance. The obstruction may be transient or permanent.

The "interstitial lung diseases (ILDs)" are a group of conditions involving the alveolar walls, perialveolar tissues, and contiguous supporting structures. As discussed on the website of the American Lung Association, the tissue between the air sacs of the lung is the interstitium, and this is the tissue affected by fibrosis in the disease. Persons with the disease have difficulty breathing in because of the stiffness of the lung tissue but, in contrast to persons with obstructive lung disease, have no difficulty breathing out. The definition, diagnosis and treatment of interstitial lung diseases are well known in the art and discussed in detail by, for example, Reynolds, H. Y., in Harrison's Principles of Internal Medicine, supra, at pp. 1460-1466. Reynolds notes that, while ILDs have various initiating events, the immunopathological responses of lung tissue are limited and the ILDs therefore have common features.

"Idiopathic pulmonary fibrosis," or "IPF," is considered the prototype ILD. Although it is idiopathic in that the cause is not known, Reynolds, supra, notes that the term refers to a well-defined clinical entity.

"Bronchoalveolar lavage," or "BAL," is a test which permits removal and examination of cells from the lower respiratory tract and is used in humans as a diagnostic procedure for pulmonary disorders such as IPF. In human patients, it is usually performed during bronchoscopy.

"Inhibition", "inhibits", "inhibiting" and "inhibitor" refer to a compound that prohibits or a method of prohibiting, a specific action or function.

The term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

The term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The term "pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

The terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

II. General

The present invention derives from the discovery that 1,3-disubstituted ureas (or the corresponding amides or carbamates, also referred to as the primary pharmacophore) can be further functionalized to provide more potent sEH inhibitors with improved physical properties. As described herein, the introduction of a heterocyclic moiety can increase water solubility and oral availability of sEH inhibitors. The combination of these moieties provides a variety of compounds of increased water solubility.

The discovery of the heterocyclic pharmacophores has also led to the employment of combinatorial chemistry approaches for establishing a wide spectrum of compounds having sEH inhibitory activity. The polar pharmacophores divide the molecule into domains each of which can be easily manipulated by common chemical approaches in a combinatorial manner, leading to the design and confirmation of novel orally available therapeutic agents for the treatment of diseases such as hypertension and vascular inflammation. The agents of the present invention treat such diseases while simultaneously increasing sodium excretion, reducing vascular and renal inflammation, and reducing male erectile dysfunction As shown below (see Examples and Figures), alterations in solubility, bioavailability and pharmacological properties leads to compounds that can alter the regulatory lipids of experimental animals increasing the relative amounts of epoxy arachidonate derivatives when compared either to their diol products or to the proinflammatory and hypertensive hydroxyeicosatetraenoic acids (HETEs). Since epoxy arachidonates are anti-hypertensive and anti-inflammatory, altering the lipid ratios can lead to reduced blood pressure and reduced vascular and renal inflammation. This approach has been validated as reported in U.S. patent application Ser. Nos. 10/817,334 and 11/256,685 which are herein incorporated by reference in their entirety.

The heterocyclic group improves water solubility of sEH inhibitors as well as the specificity for the sEH, and a wide diversity of functionalities such as an ester, amide, carbamate, or similar functionalities capable of donating or accepting a hydrogen bond similarly can contribute to this polar group. For example, in pharmaceutical chemistry heterocyclic groups are commonly used to mimic carbonyls as hydrogen bond donors and acceptors. Of course the primary, secondary and tertiary pharmacophore groups can be combined in a single molecule with suitable spacers to improve activity or present the inhibitor as a prodrug.

III. Compounds for Inhibiting Soluble Epoxide Hydrolases

In addition to the methods provided below, the present invention provides compounds that can inhibit the activity of soluble epoxide hydrolases. In particular, the present invention provides compounds having a formula selected from the formulas below. The compounds of the present invention have chemical handles that allow attachment of fluorescent molecules useful for binding studies such as fluorescence polarization or FRET. Affinity ligands can also be attached to the compounds of the present invention.

In some embodiments, the present invention provides a compound of 1-(1-(2-methylbutyryl)piperidin-4-yl)-3-(4-(trifluoromethoxy)phenyl)urea, (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, 1-(1-(2-ethylbutanoyl)piperidin-4-yl)-3-(4-(trifluoromethoxy)phenyl)urea, 1-(1-(2-ethylbutanoyl)piperidin-4-yl)-3-(4-(trifluoromethyl)phenyl)urea, (S)-1-(1-(2-methylbutanoyl)piperidin-4-yl)-3-(4-(trifluoromethoxy)phenyl)urea, 1-cyclohexyl-3-(1-(2-methylbutanoyl)piperidin-4-yl)urea, 1-cycloheptyl-3-(1-(2-methylbutanoyl)piperidin-4-yl)urea, 1-(4-isopropylphenyl)-3-(1-(2-methylbutanoyl)piperidin-4-yl)urea, 1-(3,5-di-trifluoromethylphenyl)-3-(1-(2-methylbutanoyl)piperidin-4-yl)urea, 1-(4-tert-butylphenyl)-3-(1-(2-methylbutanoyl)piperidin-4-yl)urea, 1-(4-ethylcyclohexyl)-3-(1-isobutyrylpiperidin-4-yl)urea, or salts and isomers thereof.

In some embodiments, the compound can be 1-(1-(2-methylbutyryl)piperidin-4-yl)-3-(4-(trifluoromethoxy)phenyl)urea, (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, or (S)-1-(1-(2-methylbutanoyl)piperidin-4-yl)-3-(4-(trifluoromethoxy)phenyl)urea.

In some other embodiments, the compound can be (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, or (S)-1-(1-(2-methylbutanoyl)piperidin-4-yl)-3-(4-(trifluoromethoxy)phenyl)urea.

In some embodiments, the compound can be (S)-1-(1-(2-methylbutanoyl)piperidin-4-yl)-3-(4-(trifluoromethyl)phenyl)urea. In other embodiments, the compound can be 1-(1-isobutyrylpiperidin-4-yl)-3-(4-(trifluoromethoxy)phenyl)urea. In some other embodiments, the compound can be (S)-1-(1-(2-methylbutanoyl)piperidin-4-yl)-3-(4-(trifluoromethoxy)phenyl)urea.

Certain compounds of the present invention possess asymmetric carbon atoms (optical centers) or double bonds; the racemates, diastereomers, geometric isomers and individual isomers are all intended to be encompassed within the scope of the present invention.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In some embodiments, the sEH inhibitors of the present invention have an $IC_{50}$ in a defined assay of less than 50 μM. In another embodiment, the compounds have an $IC_{50}$ of 1 μM or less. In another embodiment, the compounds have an $IC_{50}$ of 500 nM or less. In another embodiment, the compounds have an $IC_{50}$ of 150 nM or less. In another embodiment, the compounds have an $IC_{50}$ of 100 nM or less. In another embodiment, the compounds have an $IC_{50}$ of 50 nM or less. In another embodiment, the compounds have an $IC_{50}$ of 1 nM or less.

The compounds of the present invention can be prepared by a variety of methods as outlined generally in the schemes. Scheme 1 describes preparation of the urea by condensing a substituted aryl isocyanate with a protected 4-amino-piperidine, followed by deprotection of the piperidine nitrogen and reaction with a suitable group, such as a carboxylic acid, and EDCI for coupling the piperidine nitrogen and carboxylic acid.

Scheme 2 describes formation of the urea, as described in Scheme 1, but where the piperidine nitrogen is already functionalized. Scheme 3 describes a process similar to Scheme 2, but where the aryl isocyanate is generated in situ from an aryl amine and triphosgene.

Scheme 4 describes preparation sulfonyl-piperidines using the method described in Scheme 1, but where the piperidine nitrogen is modified with the sulfonyl group using a sulfonyl chloride.

IV. Pharmaceutical Compositions

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of the present invention, or a pharmaceutically acceptable salt of a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., *REMINGTON'S PHARMACEUTICAL SCIENCES*, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethyl-cellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

V. Administration

Administration of the compounds of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone.

The compositions containing a compound or a combination of compounds of the present invention may be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semisolid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a compound or a combination of compounds. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, *REMINGTON'S PHARMACEUTICAL SCIENCES*, 18TH ED., Mack Publishing Co., Easton, Pa. (1990)). The composition to be administered contains a quantity of the compound or combination of compounds in a pharmaceutically effective amount for relief of a condition being treated (e.g. osteoporosis) when administered in accordance with the teachings of this invention. In addition, pharmaceutically acceptable salts of the compounds of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4$^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the compounds or combination of compounds, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The compounds can also be formulated into a suppository disposed, for example, in a polyethylene glycol (PEG) carrier.

Liquid compositions can be prepared by dissolving or dispersing a compound or a combination of compounds and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The compounds of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Generally, administered dosages will be effective to deliver picomolar to micromolar concentrations of the compound to the appropriate site or sites. However, one of ordinary skill in the art understands that the dose administered will vary depending on a number of factors, including, but not limited to, the particular compound or set of compounds to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the compounds of the present invention permits a wider margin of safety for dosage concentrations and for repeated dosing.

The pharmaceutical compositions of the present invention can be prepared for administration by a variety of different routes. In general, the type of carrier is selected based on the mode of administration. Pharmaceutical compositions can be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal, or intraurethral injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

VI. Methods

In view of the above, the present invention provides, in one aspect, a method for inhibiting a soluble epoxide hydrolase, comprising contacting the soluble epoxide hydrolase with an inhibiting amount of a compound of the present invention.

In other embodiments, the present invention provides a method for monitoring the activity of a soluble epoxide hydrolase, the method including contacting the soluble epoxide hydrolase with an amount of a compound of the present invention sufficient to produce a detectable change in the fluorescence of the soluble epoxide hydrolase by interacting with one or more tryptophan residues present in the catalytic site of said sEH.

A. Assays to Monitor Soluble Epoxide Hydrolase Activity:

Additionally, the present invention provides a variety of assays and associated methods for monitoring soluble epoxide hydrolase activity, particularly the activity that has been modulated by the administration of one or more of the compounds provided above.

In one group of embodiments, the invention provides methods for reducing the formation of a biologically active diol produced by the action of a soluble epoxide hydrolase, the method comprising contacting the soluble epoxide hydrolase with an amount of a compound of the present invention, sufficient to inhibit the activity of the soluble epoxide hydrolase and reduce the formation of the biologically active diol.

In another group of embodiments, the invention provides methods for stabilizing biologically active epoxides in the presence of a soluble epoxide hydrolase, the method comprising contacting the soluble epoxide hydrolase with an amount of a compound of the present invention, sufficient to inhibit the activity of the soluble epoxide hydrolase and stabilize the biologically active epoxide.

In each of these groups of embodiments, the methods can be carried out as part of an in vitro assay or the methods can be carried out in vivo by monitoring blood titers of the respective biologically active epoxide or diol.

Epoxides and diols of some fatty acids are biologically important chemical mediators and are involved in several biological processes. The strongest biological data support the action of oxylipins as chemical mediators between the vascular endothelium and vascular smooth muscle. Epoxy lipids are anti-inflammatory and anti-hypertensive. Additionally, the lipids are thought to be metabolized by beta-oxidation, as well as by epoxide hydration. The soluble epoxide hydrolase is considered to be the major enzyme involved in the hydrolytic metabolism of these oxylipins. The compounds of the present invention can inhibit the epoxide hydrolase and stabilize the epoxy lipids both in vitro and in vivo. This activity results in a reduction of hypertension in four separate rodent models. Moreover, the inhibitors show a reduction in renal inflammation associated with and independent of the hypertensive models.

More particularly, the present invention provides methods for monitoring a variety of lipids in both the arachidonate and linoleate cascade simultaneously in order to address the biology of the system. A GLC-MS system or a LC-MS method can be used to monitor over 740 analytes in a highly quantitative fashion in a single injection. The analytes include the regioisomers of the arachidonate epoxides (EETs), the diols (DHETs), as well as other P450 products including HETEs. Characteristic products of the cyclooxygenase, lipoxygenase, and peroxidase pathways in both the arachidonate and linoleate series can also be monitored. Such methods are particularly useful as being predictive of certain disease states. The oxylipins can be monitored in mammals following the administration of inhibitors of epoxide hydrolase. Generally, EH inhibitors increase epoxy lipid concentrations at the expense of diol concentrations in body fluids and tissues.

Other compounds for use in this aspect of the invention are those compounds of the present invention in which the primary pharmacophore is separated from a secondary and/or tertiary pharmacophore by a distance that approximates the distance between the terminal carboxylic acid and an epoxide functional group in the natural substrate.

B. Methods of Treating Diseases Modulated by Soluble Epoxide Hydrolases:

In another aspect, the present invention provides methods of treating diseases, especially those modulated by soluble epoxide hydrolases (sEH). The methods generally involve administering to a subject in need of such treatment an effective amount of a compound of the present invention. The dose, frequency and timing of such administering will depend in large part on the selected therapeutic agent, the nature of the condition being treated, the condition of the subject including age, weight and presence of other conditions or disorders, the formulation being administered and the discretion of the attending physician. Preferably, the compositions and compounds of the invention and the pharmaceutically acceptable salts thereof are administered via oral, parenteral, subcutaneous, intramuscular, intravenous or topical routes. Generally, the compounds are administered in dosages ranging from about 2 mg up to about 2,000 mg per day, although variations will necessarily occur depending, as noted above, on the disease target, the patient, and the route of administration. Dosages are administered orally in the range of about 0.05 mg/kg to about 20 mg/kg, more preferably in the range of about 0.05 mg/kg to about 2 mg/kg, most preferably in the range of about 0.05 mg/kg to about 0.2 mg per kg of body weight per day. The dosage employed for the topical administration will, of course, depend on the size of the area being treated.

It has previously been shown that inhibitors of soluble epoxide hydrolase ("sEH") can reduce hypertension. Such inhibitors can be useful in controlling the blood pressure of persons with undesirably high blood pressure, including those who suffer from diabetes.

In some embodiments, compounds of the present invention are administered to a subject in need of treatment for hypertension, specifically renal, hepatic, or pulmonary hypertension; inflammation, specifically renal inflammation, vascular inflammation, and lung inflammation; adult respiratory distress syndrome; diabetic complications; end stage renal disease; Raynaud syndrome and arthritis.

C. Methods for Inhibiting Progression of Kidney Deterioration (Nephropathy) and Reducing Blood Pressure:

In another aspect of the invention, the compounds of the invention can reduce damage to the kidney, and especially damage to kidneys from diabetes, as measured by albuminuria. The compounds of the invention can reduce kidney deterioration (nephropathy) from diabetes even in individuals who do not have high blood pressure. The conditions of therapeautic administration are as described above.

cis-Epoxyeicosantrienoic acids ("EETs") can be used in conjunction with the compounds of the invention to further reduce kidney damage. EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into DHETs is reduced. Without wishing to be bound by theory, it is believed that raising the level of EETs interferes with damage to kidney cells by the microvasculature changes and other pathologic effects of diabetic hyperglycemia. Therefore, raising the EET level in the kidney is believed to protect the kidney from progression from microalbuminuria to end stage renal disease.

EETs are well known in the art. EETs useful in the methods of the present invention include 14,15-EET, 8,9-EET and 11,12-EET, and 5,6 EETs, in that order of preference. Preferably, the EETs are administered as the methyl ester, which is more stable. Persons of skill will recognize that the EETs are regioisomers, such as 8S,9R- and 14R,15S-EET. 8,9-EET, 11,12-EET, and 14R,15S-EET, are commercially available from, for example, Sigma-Aldrich (catalog nos. E5516, E5641, and E5766, respectively, Sigma-Aldrich Corp., St. Louis, Mo.).

EETs produced by the endothelium have anti-hypertensive properties and the EETs 11,12-EET and 14,15-EET may be endothelium-derived hyperpolarizing factors (EDHFs). Additionally, EETs such as 11,12-EET have profibrinolytic effects, anti-inflammatory actions and inhibit smooth muscle cell proliferation and migration. In the context of the present invention, these favorable properties are believed to protect the vasculature and organs during renal and cardiovascular disease states.

It is now believed that sEH activity can be inhibited sufficiently to increase the levels of EETs and thus augment the effects of administering sEH inhibitors by themselves. This permits EETs to be used in conjunction with one or more sEH inhibitors to reduce nephropathy in the methods of the invention. It further permits EETs to be used in conjunction with one or more sEH inhibitors to reduce hypertension, or inflammation, or both. Thus, medicaments of EETs can be made which can be administered in conjunction with one or more sEH inhibitors, or a medicament containing one or more sEH inhibitors can optionally contain one or more EETs.

The EETs can be administered concurrently with the sEH inhibitor, or following administration of the sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs are administered after the inhibitor is administered, therefore, it is desirable that the EETs be administered during the period during which the inhibitor will be present in amounts to be effective to delay hydrolysis of the EETs. Typically, the EET or EETs will be administered within 48 hours of administering an sEH inhibitor. Preferably, the EET or EETs are administered within 24 hours of the inhibitor, and even more preferably within 12 hours. In increasing order of desirability, the EET or EETs are administered within 10, 8, 6, 4, 2, hours, 1 hour, or one half hour after administration of the inhibitor. Most preferably, the EET or EETs are administered concurrently with the inhibitor.

In some embodiments, the EETs, the compound of the invention, or both, are provided in a material that permits them to be released over time to provide a longer duration of action. Slow release coatings are well known in the pharmaceutical art; the choice of the particular slow release coating is not critical to the practice of the present invention.

EETs are subject to degradation under acidic conditions. Thus, if the EETs are to be administered orally, it is desirable that they are protected from degradation in the stomach. Conveniently, EETs for oral administration may be coated to permit them to passage the acidic environment of the stomach into the basic environment of the intestines. Such coatings are well known in the art. For example, aspirin coated with so-called "enteric coatings" is widely available commercially. Such enteric coatings may be used to protect EETs during passage through the stomach. An exemplary coating is set forth in the Examples.

While the anti-hypertensive effects of EETs have been recognized, EETs have not been administered to treat hypertension because it was thought endogenous sEH would hydrolyse the EETs too quickly for them to have any useful effect. Surprisingly, it was found during the course of the studies underlying the present invention that exogenously administered inhibitors of sEH succeeded in inhibiting sEH sufficiently that levels of EETs could be further raised by the administration of exogenous EETs. These findings underlie the co-administration of sEH inhibitors and of EETs described above with respect to inhibiting the development and progression of nephropathy. This is an important improvement in augmenting treatment. While levels of endogenous EETs are expected to rise with the inhibition of sEH activity caused by the action of the sEH inhibitor, and therefore to result in at least some improvement in symptoms or pathology, it may not be sufficient in all cases to inhibit progression of kidney damage fully or to the extent intended. This is particularly true where the diseases or other factors have reduced the endogenous concentrations of EETs below those normally present in healthy individuals. Administration of exogenous EETs in conjunction with a sEH inhibitor is therefore expected to be beneficial and to augment the effects of the sEH inhibitor in reducing the progression of diabetic nephropathy.

The present invention can be used with regard to any and all forms of diabetes to the extent that they are associated with progressive damage to the kidney or kidney function. The chronic hyperglycemia of diabetes is associated with long-term damage, dysfunction, and failure of various organs, especially the eyes, kidneys, nerves, heart, and blood vessels. The long-term complications of diabetes include retinopathy with potential loss of vision; nephropathy leading to renal failure; peripheral neuropathy with risk of foot ulcers, amputation, and Charcot joints.

In addition, persons with metabolic syndrome are at high risk of progression to type 2 diabetes, and therefore at higher risk than average for diabetic nephropathy. It is therefore desirable to monitor such individuals for microalbuminuria, and to administer a sEH inhibitor and, optionally, one or more EETs, as an intervention to reduce the development of nephropathy. The practitioner may wait until microalbuminuria is seen before beginning the intervention. As noted above, a person can be diagnosed with metabolic syndrome without having a blood pressure of 130/85 or higher. Both persons with blood pressure of 130/85 or higher and persons with blood pressure below 130/85 can benefit from the administration of sEH inhibitors and, optionally, of one or more EETs, to slow the progression of damage to their kidneys. In some embodiments, the person has metabolic syndrome and blood pressure below 130/85.

Dyslipidemia or disorders of lipid metabolism is another risk factor for heart disease. Such disorders include an increased level of LDL cholesterol, a reduced level of HDL cholesterol, and an increased level of triglycerides. An increased level of serum cholesterol, and especially of LDL cholesterol, is associated with an increased risk of heart disease. The kidneys are also damaged by such high levels. It is believed that high levels of triglycerides are associated with kidney damage. In particular, levels of cholesterol over 200 mg/dL, and especially levels over 225 mg/dL, would suggest that sEH inhibitors and, optionally, EETs, should be administered. Similarly, triglyceride levels of more than 215 mg/dL, and especially of 250 mg/dL or higher, would indicate that administration of sEH inhibitors and, optionally, of EETs, would be desirable. The administration of compounds of the present invention with or without the EETs, can reduce the need to administer statin drugs (HMG-CoA reductase inhibitors) to the patients, or reduce the amount of the statins needed. In some embodiments, candidates for the methods, uses and compositions of the invention have triglyceride levels over 215 mg/dL and blood pressure below 130/85. In some embodiments, the candidates have triglyceride levels over 250 mg/dL and blood pressure below 130/85. In some embodiments, candidates for the methods, uses and compositions of the invention have cholesterol levels over 200 mg/dL and blood pressure below 130/85. In some embodiments, the candidates have cholesterol levels over 225 mg/dL and blood pressure below 130/85.

D. Methods of Inhibiting the Proliferation of Vascular Smooth Muscle Cells:

In other embodiments, compounds of the present invention inhibit proliferation of vascular smooth muscle (VSM) cells without significant cell toxicity, (e.g., specific to VSM cells). Because VSM cell proliferation is an integral process in the pathophysiology of atherosclerosis, these compounds are suitable for slowing or inhibiting atherosclerosis. These compounds are useful to subjects at risk for atherosclerosis, such as individuals who have had a heart attack or a test result showing decreased blood circulation to the heart. The conditions of therapeutic administration are as described above.

The methods of the invention are particularly useful for patients who have had percutaneous intervention, such as angioplasty to reopen a narrowed artery, to reduce or to slow the narrowing of the reopened passage by restenosis. In some embodiments, the artery is a coronary artery. The compounds of the invention can be placed on stents in polymeric coatings to provide a controlled localized release to reduce restenosis. Polymer compositions for implantable medical devices, such as stents, and methods for embedding agents in the polymer for controlled release, are known in the art and taught, for example, in U.S. Pat. Nos. 6,335,029; 6,322,847; 6,299,604; 6,290,722; 6,287,285; and 5,637,113. In some embodiments, the coating releases the inhibitor over a period of time, preferably over a period of days, weeks, or months. The particular polymer or other coating chosen is not a critical part of the present invention.

The methods of the invention are useful for slowing or inhibiting the stenosis or restenosis of natural and synthetic vascular grafts. As noted above in connection with stents, desirably, the synthetic vascular graft comprises a material which releases a compound of the invention over time to slow or inhibit VSM proliferation and the consequent stenosis of the graft. Hemodialysis grafts are a particular embodiment.

In addition to these uses, the methods of the invention can be used to slow or to inhibit stenosis or restenosis of blood vessels of persons who have had a heart attack, or whose test results indicate that they are at risk of a heart attack.

In one group of embodiments, compounds of the invention are administered to reduce proliferation of VSM cells in persons who do not have hypertension. In another group of embodiments, compounds of the invention are used to reduce proliferation of VSM cells in persons who are being treated for hypertension, but with an agent that is not an sEH inhibitor.

The compounds of the invention can be used to interfere with the proliferation of cells which exhibit inappropriate cell cycle regulation. In one important set of embodiments, the cells are cells of a cancer. The proliferation of such cells can be slowed or inhibited by contacting the cells with a compound of the invention. The determination of whether a particular compound of the invention can slow or inhibit the proliferation of cells of any particular type of cancer can be determined using assays routine in the art.

In addition to the use of the compounds of the invention, the levels of EETs can be raised by adding EETs. VSM cells contacted with both an EET and a compound of the invention exhibited slower proliferation than cells exposed to either the EET alone or to the a compound of the invention alone. Accordingly, if desired, the slowing or inhibition of VSM cells of a compound of the invention can be enhanced by adding an EET along with a compound of the invention. In the case of stents or vascular grafts, for example, this can conveniently be accomplished by embedding the EET in a coating along with a compound of the invention so that both are released once the stent or graft is in position.

E. Methods of Inhibiting the Progression of Obstructive Pulmonary Disease, Interstitial Lung Disease, or Asthma:

Chronic obstructive pulmonary disease, or COPD, encompasses two conditions, emphysema and chronic bronchitis, which relate to damage caused to the lung by air pollution, chronic exposure to chemicals, and tobacco smoke. Emphysema as a disease relates to damage to the alveoli of the lung, which results in loss of the separation between alveoli and a consequent reduction in the overall surface area available for gas exchange. Chronic bronchitis relates to irritation of the bronchioles, resulting in excess production of mucin, and the consequent blocking by mucin of the airways leading to the alveoli. While persons with emphysema do not necessarily have chronic bronchitis or vice versa, it is common for persons with one of the conditions to also have the other, as well as other lung disorders.

Some of the damage to the lungs due to COPD, emphysema, chronic bronchitis, and other obstructive lung disorders can be inhibited or reversed by administering inhibitors of the enzyme known as soluble epoxide hydrolase, or "sEH". The effects of sEH inhibitors can be increased by also administering EETs. The effect is at least additive over administering the two agents separately, and may indeed be synergistic.

The studies reported herein show that EETs can be used in conjunction with sEH inhibitors to reduce damage to the lungs by tobacco smoke or, by extension, by occupational or environmental irritants. These findings indicate that the co-administration of sEH inhibitors and of EETs can be used to inhibit or slow the development or progression of COPD, emphysema, chronic bronchitis, or other chronic obstructive lung diseases which cause irritation to the lungs.

Animal models of COPD and humans with COPD have elevated levels of immunomodulatory lymphocytes and neutrophils. Neutrophils release agents that cause tissue damage and, if not regulated, will over time have a destructive effect. Without wishing to be bound by theory, it is believed that reducing levels of neutrophils reduces tissue damage contributing to obstructive lung diseases such as COPD, emphysema, and chronic bronchitis. Administration of sEH inhibitors to rats in an animal model of COPD resulted in a reduction in the number of neutrophils found in the lungs. Administration of EETs in addition to the sEH inhibitors also reduced neutrophil levels. The reduction in neutrophil levels in the presence of sEH inhibitor and EETs was greater than in the presence of the sEH inhibitor alone.

While levels of endogenous EETs are expected to rise with the inhibition of sEH activity caused by the action of the sEH inhibitor, and therefore to result in at least some improvement in symptoms or pathology, it may not be sufficient in all cases to inhibit progression of COPD or other pulmonary diseases. This is particularly true where the diseases or other factors have reduced the endogenous concentrations of EETs below those normally present in healthy individuals. Administration of exogenous EETs in conjunction with an sEH inhibitor is therefore expected to augment the effects of the sEH inhibitor in inhibiting or reducing the progression of COPD or other pulmonary diseases.

In addition to inhibiting or reducing the progression of chronic obstructive airway conditions, the invention also provides new ways of reducing the severity or progression of chronic restrictive airway diseases. While obstructive airway diseases tend to result from the destruction of the lung parenchyma, and especially of the alveoli, restrictive diseases tend to arise from the deposition of excess collagen in the parenchyma. These restrictive diseases are commonly referred to as "interstitial lung diseases", or "ILDs", and include conditions such as idiopathic pulmonary fibrosis. The methods, compositions and uses of the invention are useful for reducing the severity or progression of ILDs, such as idiopathic pulmonary fibrosis. Macrophages play a significant role in stimulating interstitial cells, particularly fibroblasts, to lay down collagen. Without wishing to be bound by theory, it is believed that neutrophils are involved in activating macrophages, and that the reduction of neutrophil levels found in the studies reported herein demonstrate that the methods and uses of the invention will also be applicable to reducing the severity and progression of ILDs.

In some embodiments, the ILD is idiopathic pulmonary fibrosis. In other embodiments, the ILD is one associated with an occupational or environmental exposure. Exemplars of such ILDs, are asbestosis, silicosis, coal worker's pneumoconiosis, and berylliosis. Further, occupational exposure to any of a number of inorganic dusts and organic dusts is believed to be associated with mucus hypersecretion and respiratory disease, including cement dust, coke oven emissions, mica, rock dusts, cotton dust, and grain dust (for a more complete list of occupational dusts associated with these conditions, see Table 254-1 of Speizer, "Environmental Lung Diseases," Harrison's Principles of Internal Medicine, infra, at pp. 1429-1436). In other embodiments, the ILD is sarcoidosis of the lungs. ILDs can also result from radiation in medical treatment, particularly for breast cancer, and from connective tissue or collagen diseases such as rheumatoid arthritis and systemic sclerosis. It is believed that the methods, uses and compositions of the invention can be useful in each of these interstitial lung diseases.

In another set of embodiments, the invention is used to reduce the severity or progression of asthma. Asthma typically results in mucin hypersecretion, resulting in partial airway obstruction. Additionally, irritation of the airway results in the release of mediators which result in airway obstruction. While the lymphocytes and other immunomodulatory cells recruited to the lungs in asthma may differ from those recruited as a result of COPD or an ILD, it is expected that the invention will reduce the influx of immunomodulatory cells, such as neutrophils and eosinophils, and ameliorate the extent of obstruction. Thus, it is expected that the administration of sEH inhibitors, and the administration of sEH inhibitors in combination with EETs, will be useful in reducing airway obstruction due to asthma.

In each of these diseases and conditions, it is believed that at least some of the damage to the lungs is due to agents released by neutrophils which infiltrate into the lungs. The presence of neutrophils in the airways is thus indicative of continuing damage from the disease or condition, while a reduction in the number of neutrophils is indicative of reduced damage or disease progression. Thus, a reduction in the number of neutrophils in the airways in the presence of an agent is a marker that the agent is reducing damage due to the disease or condition, and is slowing the further development of the disease or condition. The number of neutrophils present in the lungs can be determined by, for example, bronchoalveolar lavage.

F. Prophylatic and Therapeutic Methods to Reduce Stroke Damage

Inhibitors of soluble epoxide hydrolase ("sEH") and EETs administered in conjunction with inhibitors of sEH have been shown to reduce brain damage from strokes. Based on these results, we expect that inhibitors of sEH taken prior to an ischemic stroke will reduce the area of brain damage and will likely reduce the consequent degree of impairment. The reduced area of damage should also be associated with a faster recovery from the effects of the stroke.

While the pathophysiologies of different subtypes of stroke differ, they all cause brain damage. Hemorrhagic stroke differs from ischemic stroke in that the damage is largely due to compression of tissue as blood builds up in the confined space within the skull after a blood vessel ruptures, whereas in ischemic stroke, the damage is largely due to loss of oxygen supply to tissues downstream of the blockage of a blood vessel by a clot. Ischemic strokes are divided into thrombotic strokes, in which a clot blocks a blood vessel in the brain, and embolic strokes, in which a clot formed elsewhere in the body is carried through the blood stream and blocks a vessel there. But, in both hemorrhagic stroke and ischemic stroke, the damage is due to the death of brain cells. Based on the results observed in our studies, however, we would expect at least some reduction in brain damage in all types of stroke and in all subtypes.

A number of factors are associated with an increased risk of stroke. Given the results of the studies underlying the present invention, sEH inhibitors administered to persons with any one or more of the following conditions or risk factors: high blood pressure, tobacco use, diabetes, carotid artery disease, peripheral artery disease, atrial fibrillation, transient ischemic attacks (TIAs), blood disorders such as high red blood cell counts and sickle cell disease, high blood cholesterol, obesity, alcohol use of more than one drink a day for women or two drinks a day for men, use of cocaine, a family history of stroke, a previous stroke or heart attack, or being elderly, will reduce the area of brain damaged of a stroke. With respect to being elderly, the risk of stroke increases for every 10 years. Thus, as an individual reaches 60, 70, or 80, administration of sEH inhibitors has an increasingly larger potential benefit. As noted in the next section, the administration of EETs in combination with one or more sEH inhibitors can be beneficial in further reducing the brain damage. One can expect beneficial effects from sEHI with or without EETs in a variety of diseases which lead to ischemia reperfusion injury such as heart attacks.

In some uses and methods, the sEH inhibitors and, optionally, EETs, are administered to persons who use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

Clot dissolving agents, such as tissue plasminogen activator (tPA), have been shown to reduce the extent of damage from ischemic strokes if administered in the hours shortly after a stroke. tPA, for example, is approved by the FDA for use in the first three hours after a stroke. Thus, at least some of the brain damage from a stroke is not instantaneous, but occurs over a period of time or after a period of time has elapsed after the stroke. It is therefore believed that administration of sEH inhibitors, optionally with EETs, can also reduce brain damage if administered within 6 hours after a stroke has occurred, more preferably within 5, 4, 3, or 2 hours after a stroke has occurred, with each successive shorter interval being more preferable. Even more preferably, the inhibitor or inhibitors are administered 2 hours or less or even 1 hour or less after the stroke, to maximize the reduction in brain damage. Persons of skill are well aware of how to make a diagnosis of whether or not a patient has had a stroke. Such determinations are typically made in hospital emergency rooms, following standard differential diagnosis protocols and imaging procedures.

In some uses and methods, the sEH inhibitors and, optionally, EETs, are administered to persons who have had a stroke within the last 6 hours who: use tobacco, have carotid artery disease, have peripheral artery disease, have atrial fibrillation, have had one or more transient ischemic attacks (TIAs), have a blood disorder such as a high red blood cell count or sickle cell disease, have high blood cholesterol, are obese, use alcohol in excess of one drink a day if a woman or two drinks a day if a man, use cocaine, have a family history of stroke, have had a previous stroke or heart attack and do not have high blood pressure or diabetes, or are 60, 70, or 80 years of age or more and do not have hypertension or diabetes.

The conditions of therapeutic administration for all of these indications are as described above.

The following examples are provided to illustrate the invention and are not intended to limit any aspect of the invention as set forth above or in the claims below.

VII. Examples

General

All reagents and solvent were purchased from Fishersci, Arcos Organics, TCI America and Aldrich and were used directly without further purifications. All syntheses were carried out in a dry nitrogen atmosphere unless otherwise specified.

Reactions were monitored by thin-layer chromatography (TLC, on Merck $F_{254}$ silica gel 60 aluminum sheets, spots were either visible under light or UV-light (254 mm) or treated with an oxidizing solution ($KMnO_4$ stain) Column chromatography was performed with Silicycle silica gel 60.

$^1$H-NMR spectra were recorded on a Varian QE-300 spectrometer at 300 MHz with deuterated chloroform ($CDCl_3$; $\partial$=7.24 ppm) or deuterated dimethyl sulfoxide (d6-DMSO) as an internal standard. $^{13}$C-NMR spectra were recorded on a Varian QE-300 spectrometer at 75 MHz and $^{19}$F-NMR spectra were recorded on a Varian QE-300 spectrometer at 282.4 MHz.

Synthetic Method 1

Step 1. Corresponding isocyanate (1 eq.) and 4-amino-1-Boc-piperidine (1.1 eq.) was dissolved in $CH_2Cl_2$ (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography yielding corresponding Boc-protected urea.

Step 2. The Boc protected urea from the step 1 was dissolved in HCl solution (2M, MeOH). The resulting solution was refluxed for 2 h. The solvent was removed under vacuo and the crude was basified to pH 12 by NaOH solution (6N). The precipitates were filtered and dried under high vacuum. The final product unprotected urea was served as a scaffold for the next step synthesis.

Step 3. Unless specified, the unprotected urea (1 eq.) from step 2, EDCI (1.5 eq.), DMAP (1.5 eq.) and corresponding carboxylic acid (1.5 eq.) was dissolved in $CH_2Cl_2$ and was stirred overnight. The reaction was quenched by addition of HCl solution (1M). The organic layer was collected and the aqueous layer was extracted with EtOAc for 4 times. The combined organic layer was concentrated under vacuo and further purified by flash chromatography.

Synthetic Method 2

Corresponding isocyanate (1 eq.) was added to a suspension of targeted piperidine (1.1 eq.) in $CH_2Cl_2$ (100 mL). The reaction was stirred overnight at rt. The reaction was quenched with the addition of HCl solution (2M, 50 mL). The organic layer was collected and the aqueous layer was further extracted with EtOAc three times. The combined organic layers was washed with sat. NaCl solution. The organic layers was concentrated under vacuo. The product was purified by flash chromatography.

Synthetic Method 3

Corresponding amine (1 eq.) and triethyl amine (1.2 eq.) was dissolved in $CH_2Cl_2$ and stirred at −78° C. Triphosgene (0.37 eq.) dissolved in $CH_2Cl_2$ was added dropwise at −78° C. The reaction was then warm to rt and was stirred for 30 min. The reaction was cooled to 0° C. Corresponding piperidine (1.1 eq.) dissolved in $CH_2Cl_2$ was added slowly and the reaction was further stirred at rt for 12 h. The reaction was quenched with the addition of HCl solution (2M, 50 mL). The organic layer was collected and the aqueous layer was further extracted with EtOAc three times. The combined organic layers was washed with sat. NaCl solution. The organic layers was concentrated under vacuo. The product was purified by flash chromatography.

Synthetic Method 4

The first two steps is the same as Method 1 unless specified.

Step 3. The unprotected urea (1 eq.) and $Et_3N$ (1.2 eq.) was dissolved in $CH_2Cl_2$ and Corresponding sulfonyl chloride was added dropwisely at 0° C. and the reaction was stirred overnight at rt. The reaction was quenched by addition of HCl solution (1M). The organic layer was collected and the aqueous layer was extracted with EtOAc for 4 times. The combined organic layer was concentrated under vacuo and further purified by flash chromatography.

Log P Determination. Octanol-water partition coefficients were determined by an HPLC method following OECD guideline 117. The accepted error for this method is ±0.5 of shake flask values. Isocratic MeOH:$H_2O$ (3:1, v/v), 50 mM ammonium acetate in MeOH:$H_2O$ (3:1, v/v) adjusted to pH 9.0, and MeOH:$H_2O$ (3:1, v/v) adjusted to pH 3.0 with $H_3PO_4$ were used for neutral, basic and acidic analytes, respectively, with a flow rate of 0.75 mL/min. The HPLC method was validated using compounds 24 and 54, which were found to have log P values of 1.9 and 2.3, respectively, using the shake flask method (OECD guideline 107).

Purity Determination.

Final products were dissolved in MeOH:$H_2O$ (3:1, v/v) at 10 μg/mL, and 100 μL injections were analyzed in triplicate by HPLC-UV with detection at 210 nm, 230 nm, 254 nm and 290 nm. HPLC conditions were the same as those for log P determination. Purity was judged as the percent of total peak area for each wavelength. The lowest observed purity is reported. Compounds were also judged to be pure based on thin layer chromatography visualized with short wave UV and stained with basic potassium permanganate.

Example 1

Synthesis of tert-butyl 4-(3-(4-(trifluoromethyl)phenyl)ureido)piperidine-1-carboxylate (1)

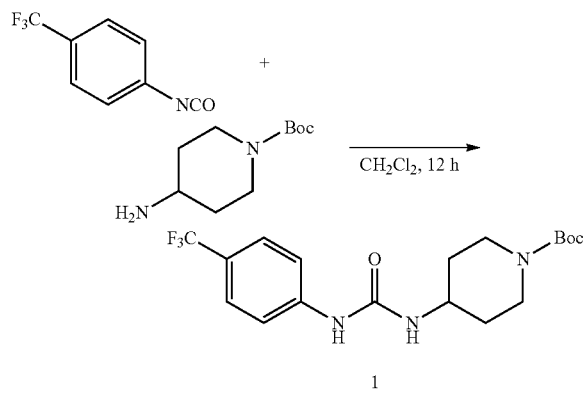

4-(Trifluoromethyl)phenyl isocyanate (1.068 g, 5.71 mmol) and 4-amino-1-Boc-piperidine (1.0 g, 5 mmol) was dissolved in $CH_2Cl_2$ (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography (EtOAc:Hex/1:1) yielding final product (1) (1.7 g, 4.39 mmol, 88%). $^1H$ NMR ($d_6$-DMSO, 300 Mhz): ∂ 8.77 (s, 1H), 7.55 (s, 4H), 6.26 (d, J=10 Hz, 1H), 3.80 (d, J=Hz, 2H), 3.64 (m, 1H), 2.88 (br, 2H), 1.78 (d, J=5 Hz, 2H), 1.38 (s, 9H), 1.23 (m, 2H).

Example 2

Synthesis of 1-(piperidin-4-yl)-3-(4-(trifluoromethyl)phenyl)urea (2)

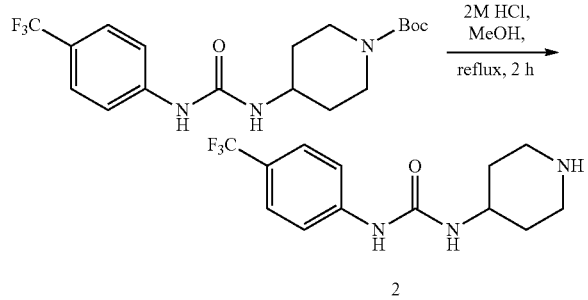

tert-butyl 4-(3-(4-(trifluoromethyl)phenyl)ureido)piperidine-1-carboxylate (1.6 g, 4.13 mmol) was dissolved in HCl solution (2 M, MeOH, 100 mL). The resulting solution was refluxed for 2 h. The solvent was removed under vacuo and the crude was basified to pH 12 by NaOH solution (6N). The final precipitates (0.9 g, 3.13 mmol, 78%) were filtered and dried under high vacuum. The final product (PTU/2) was served as a scaffold for the following urea inhibitors synthesis. $^1H$ NMR ($d_6$-DMSO, 300 Mhz): ∂ 8.77 (s, 1H), 7.57 (s, 4H), 6.30 (d, J=7.8 Hz, 1H), 3.55 (m, 1H), 2.91 (d, J=12.6 Hz, 2H), 2.48 (d, J=11.1 Hz, 2H), 1.77 (d, J=11 Hz, 2H), 1.22 (m, 2H).

Example 3

Synthesis of tert-butyl 4-(3-(4-(trifluoromethoxy)phenyl)ureido)piperidine-1-carboxylate (3)

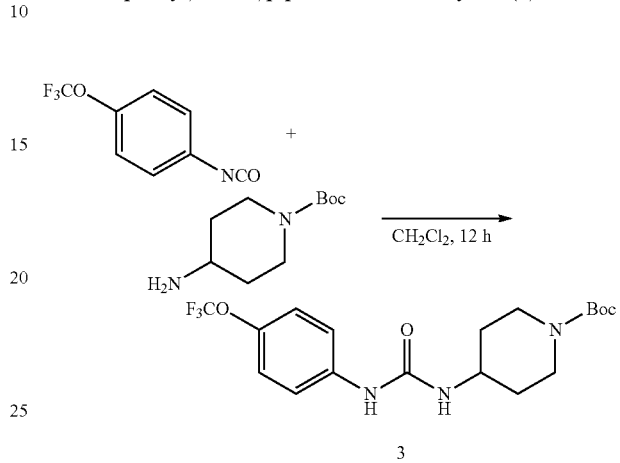

4-(Trifluoromethoxy)phenyl isocyanate (4 g, 19.7 mmol) and 4-amino-1-Boc-piperidine (4.3 g, 21.7 mmol) was dissolved in $CH_2Cl_2$ (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography (EtOAc:Hex/1:1) yielding final product (1) (7.5 g, 18.6 mmol, 94%). $^1H$ NMR ($d_6$-DMSO, 300 Mhz): ∂ 1.24 (m, 2H), 1.40 (s, 9H), 1.76 (m, 2H), 2.89 (br, 2H), 3.63 (m, 1H), 3.80 (d, J=12 Hz, 2H), 6.22 (d, J=8 Hz, 1H), 7.21 (d, J=9 Hz, 2H), 7.47 (d, J=9 Hz, 2H), 8.54 (s, 1H). $^{19}F$ NMR ($d_6$-DMSO, 300 Mhz): ∂ 57.17.

Example 4

Synthesis of 1-(piperidin-4-yl)-3-(4-(trifluoromethoxy)phenyl)urea (4)

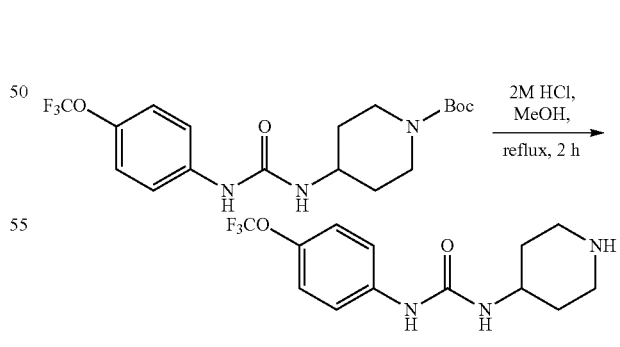

tert-butyl 4-(3-(4-(trifluoromethoxy)phenyl)ureido)piperidine-1-carboxylate (7.5 g, 18.6 mmol) was dissolved in HCl solution (2 M, MeOH, 100 mL). The resulting solution was refluxed for 2 h. The solvent was removed under vacuo and the crude was washed by dichloromethane twice and was basified to pH 10 by NaOH solution (6N). The final precipitates (5.6 g, 18.5 mmol, 99%) were filtered and dried under high vacuum. The final product (PTU/2) was served as a scaffold for the following urea inhibitors synthesis. $^1$H NMR (d$_6$-DMSO, 300 Mhz): ∂ 1.19 (m, 2H), 1.74 (d, J=9 Hz, 2H), 2.10 (br, 1H), 2.48 (m, 2H), 2.87 (d, J=9 Hz, 2H), 2.90 (m, 1H), 6.18 (d, J=8 Hz, 1H), 7.20 (d, J=9 Hz, 2H), 7.46 (d, J=9 Hz, 2H), 8.52 (s, 1H). $^{19}$F NMR (d$_6$-DMSO, 300 Mhz): ∂ 57.17.

Example 5

Synthesis of 1-(1-isobutyrylpiperidin-4-yl)-3-(4-(trifluoromethyl)phenyl)urea (5)

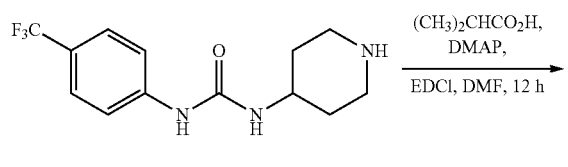

2

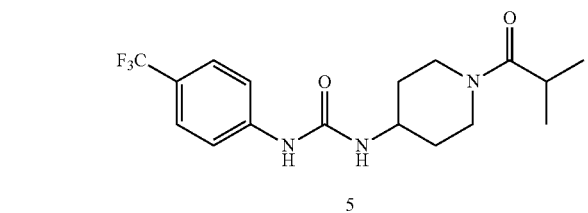

5

Isobutyric acid (37 mg, 0.418 mmol), DMAP (51 mg, 0.418 mmol) and EDCI (59 mg, 0.334 mmol) was dissolved in DMF (10 mL). PTU (80 mg, 0.278 mmol) was dissolved in DMF (5 mL) and was added into the reaction mixture dropwisely. The reaction mixture was stirred for 12 h and was quenched by addition of HCl solution (1M). The organic layer was collected and the aqueous layer was extracted with EtOAc for 4 times. The combined organic layer was concentrated under vacuo and further purified by flash chromatography (EtOAc:Hex/1:1) yielding final product (90 mg, 0.252 mmol, 90% yield). $^1$H NMR (d$_6$-DMSO, 300 Mhz): ∂ 8.79 (s, 1H), 7.57 (s, 4H), 6.38 (d, J=7.8 Hz, 1H), 4.25 (d, J=Hz, 1H), 3.85 (d, J=12.6 Hz, 1H), 3.75 (m, 1H), 3.18 (t, J=Hz, 1H), 2.85 (m, J=Hz, 1H), 2.79 (t, J=Hz, 1H), 1.85 (t, J=Hz, 2H), 1.25 (m, J, =Hz, 2H), 0.98 (s, 6H).

Example 6

Synthesis of 1-(1-butyrylpiperidin-4-yl)-3-(4-(trifluoromethyl)phenyl)urea (6)

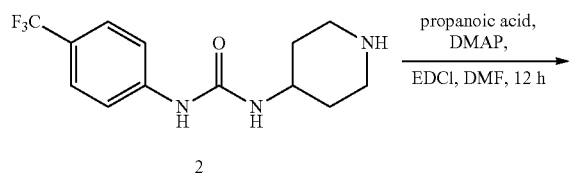

2

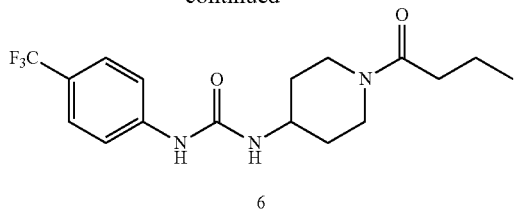

6

This synthesis of 6 follows Method 1. Butyric acid (37 mg, 0.418 mmol) was used and the product was purified by flash chromatography using (EtOAc:Hex/1:1) and yielding final product (91 mg, 0.255 mmol, 91% yield). $^1$H NMR (d$_6$-DMSO, 300 Mhz): ∂ 8.79 (s, 1H), 7.56 (s, 4H), 6.36 (d, J=7.8 Hz, 1H), 4.19 (d, J=12.9 Hz, 1H), 3.75 (d, J=14.4 Hz, 1H), 3.12 (t, J=11.4 Hz, 1H), 2.77 (m, J=12 Hz, 1H), 2.28 (t, J=7.5 Hz, 2H), 1.82 (t, J=13.2 Hz, 2H), 1.49 (m, 2H), 1.29 (m, 3H), 0.88 (t, J=7.5 Hz, 3H).

Example 7

Synthesis of 1-(1-(3,3,3-trifluoropropionyl)piperidin-4-yl)-3-(4-(trifluoromethyl)phenyl)urea (7)

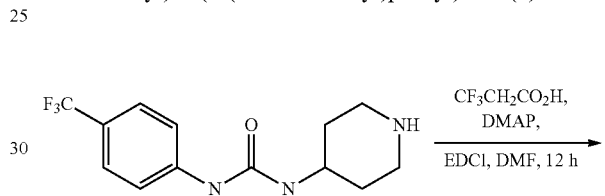

2

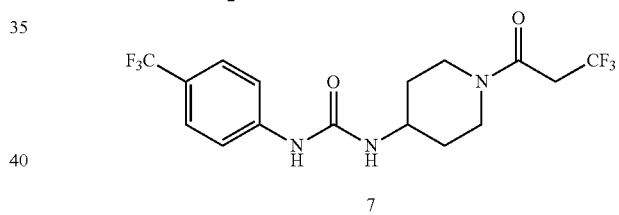

7

This synthesis of 7 follows Method 1. 3,3,3-Trifluoropropionic acid (67 mg, 0.522 mmol) was used and the product was purified by flash chromatography using (EtOAc:Hex/8:2) and yielding final (120 mg, 0.302 mmol, 87% yield). $^1$H NMR (d$_6$-DMSO, 300 Mhz): ∂ 8.80 (s, 1H), 7.58 (s, 4H), 6.38 (d, J=7.8 Hz, 1H), 4.19 (d, J=13.3 Hz, 1H), 3.79 (d, J=13.8 Hz, 1H), 3.71 (m, 4H), 3.16 (t, J=11.1 Hz, 1H), 2.85 (t, J=11.7 Hz, 1H), 1.84 (m, 2H), 1.30 (m, 2H). Melting point: 209.2-210.7 (210.3).

Example 8

Synthesis of 1-(1-(2-methylbutyryl)piperidin-4-yl)-3-(4-(trifluoromethyl)phenyl)urea (8)

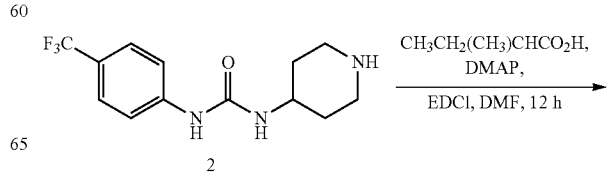

2

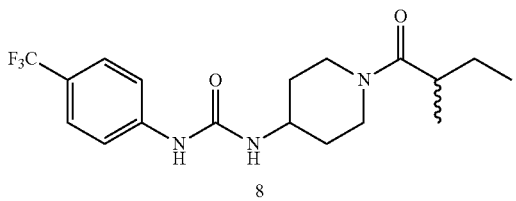

8

The synthesis of 8 follows Method 1. 2-Methylbutyric acid (50 mg, 0.487 mmol) was used and the product was purified by flash chromatography using (EtOAc:Hex/7:3) and further purified by recrystallization using methanol and water yielding the final product (65 mg, 0.175 mmol, 72% yield). $^1$H NMR (d$_6$-DMSO, 300 Mhz): ∂ 8.77 (d, J=8.4 Hz, 1H), 7.57 (s, 4H), 6.37 (s, 1H), 4.22 (m, 1H), 3.88 (d, J=13.2 Hz, 1H), 3.71 (m, 1H), 3.17 (t, J=12.8 Hz, 1H), 2.84 (m, 2H), 1.85 (m, 2H), 1.54 (m, 1H), 1.29 (m, 3H), 0.97 (s, 3H), 0.81 (d, J=6 Hz, 3H).

Example 9

Synthesis of 1-(1-(cyclopropanecarbonyl)piperidin-4-yl)-3-(4-(trifluoromethyl)phenyl)urea (9)

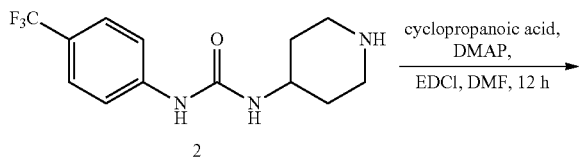

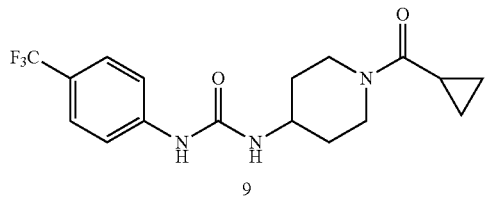

9

The synthesis of 9 follows Method 1. Cyclopropanoic acid (36 mg, 0.418 mmol) was used and the product was purified by flash chromatography using (EtOAc:Hex/9:1) and further purified by recrystallization using methanol and water yielding the final product (100 mg, 0.282 mmol, 81% yield). $^1$H NMR (d$_6$-DMSO, 300 Mhz): ∂ 8.80 (s, 1H), 7.57 (s, 4H), 6.37 (d, J=7.2 Hz, 1H), 4.16 (br, 2H), 3.74 (m, 1H), 3.25 (t, J=11.7 Hz, 1H), 2.81 (t, J=10.8 Hz, 1H), 1.98 (m, 1H), 1.85 (m, 2H), 1.30 (m, 2H), 0.7 (s, 41-1). Melting point: 193.4-194.2 (193.7).

Example 10

Synthesis of 1-(1-(4,4,4-trifluorobutanoyl)piperidin-4-yl)-3-(4-(trifluoromethyl)phenyl)urea (10)

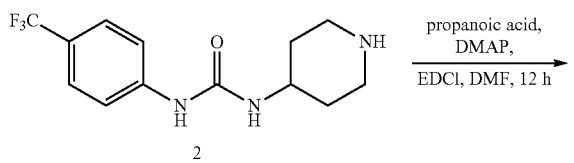

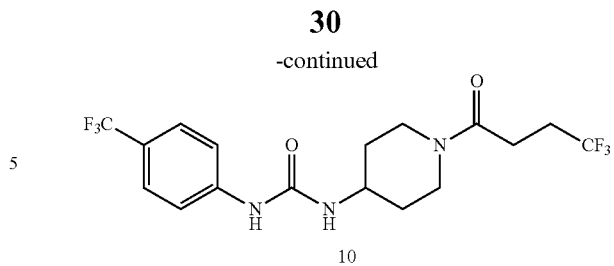

10

The synthesis of 10 follows Method 1. Cyclopropanoic acid (36 mg, 0.418 mmol) was used and the product was purified by flash chromatography using (EtOAc:Hex/9:1) and further purified by recrystallization using methanol and water yielding the final product (100 mg, 0.282 mmol, 81% yield). $^1$H NMR (d$_6$-DMSO, 300 Mhz): ∂ 8.80 (s, 1H), 7.58 (s, 4H), 6.38 (d, J=7.8 Hz, 1H), 4.19 (d, J=13.8 Hz, 1H), 3.79 (d, J=13.8 Hz, 1H), 3.77 (m, 1H), 3.16 (t, J=12.3 Hz, 1H), 2.84 (m, J=11.4 Hz, 1H), 2.60 (d, J=6.3 Hz, 2H), 2.59 (m, 2H), 1.85 (br, 2H), 1.30 (m, 2H). Melting point: 193.4-194.2 (193.7).

Example 11

Synthesis of (S)-1-(1-(2-methylbutanoyl)piperidin-4-yl)-3-(4-(trifluoromethyl)phenyl)urea (11)

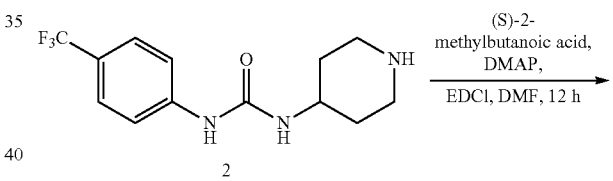

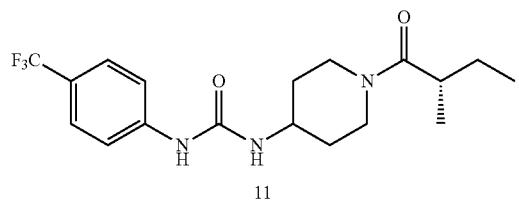

11

The synthesis of 11 follows Method 1. (S)-2-methyl butanoic acid (50 mg, 0.490 mmol) was used and the product was purified by flash chromatography using (EtOAc:Hex/8:2) and further purified by recrystallization using methanol and water yielding the final product (96 mg, 0.258 mmol, 93% yield). $^1$H NMR (d$_6$-DMSO, 300 Mhz): ∂ ∂ 0.81 (q, J=6 Hz, 3H), 0.97 (t, J=6 Hz, 3H), 1.28 (m, 3H), 1.54 (m, 1H), 1.85 (m, 2H), 2.71 (m, 2H), 2.80 (m, 1H), 3.17 (t, J=12 Hz, 1H), 3.73 (m, 1H), 3.88 (d, 1=12 Hz, 1H, 4.22 (m, 1H), 6.36 (t, J=7 Hz, 1H), 7.57 (s, 4H), 8.7 (d, J=8 Hz, 1H). F-NMR (DMSO-d$_6$) ∂ −60.0. HRMS (calculated for [H$^+$]: C$_{18}$H$_{24}$F$_3$N$_3$O$_2$): 372.1899. found (ESI(+), [M-H$^+$]): 372.1840. Melting point: 221.3-225.6 (221.6).

Example 12

Synthesis of (S)-1-(1-(2-methylbutanoyl)piperidin-4-yl)-3-(4-(trifluoromethoxy)phenyl)urea (13)

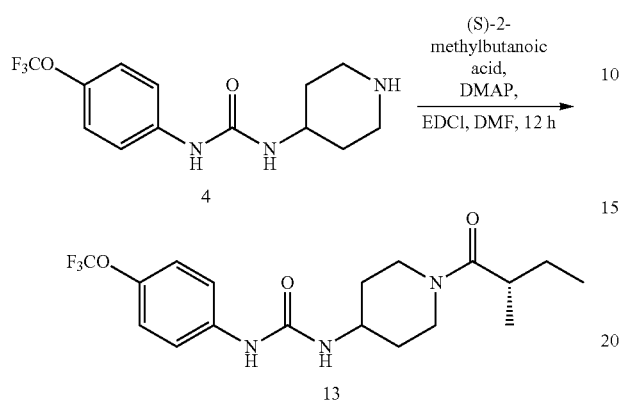

The synthesis of 13 follows Method 1. (S)-2-methyl butanoic acid (50 mg, 0.49 mmol) was used and the product was purified by flash chromatography using (EtOAc:Hex/8:2) and further purified by recrystallization using methanol and water yielding the final product (89 mg, 0.230 mmol, 83% yield). H-NMR (DMSO-$d_6$) ∂ 0.80 (d, J=6 Hz, 3H), 0.97 (s, 3H), 1.28 (m, 3H), 1.53 (m, 2H), 1.84 (tbr, 2H), 2.73 (m, 1H), 2.79 (m, 1H), 3.16 (t, J=12 Hz, 1H), 3.70 (m, 1H), 3.88 (d, J=12 Hz, 1H), 4.22 (br, 1H), 6.26 (tbr, 1H), 7.22 (d, J=9 Hz, 2H), 7.48 (d, J=9 Hz, 2H), 8.54 (d, J=9 Hz, 1H). F-NMR (DMSO-$d_6$) ∂ −57.17. HRMS (calculated for [H$^+$]: $C_{18}H_{22}F_3N_3O_3$): 388.1848. found (ESI(+), [M-H$^+$]): 388.1837. Melting point: 168.0-169.3 (168.7).

Example 13

Synthesis of 1-(1-isobutyrylpiperidin-4-yl)-3-(4-(trifluoromethoxy)phenyl)urea (14)

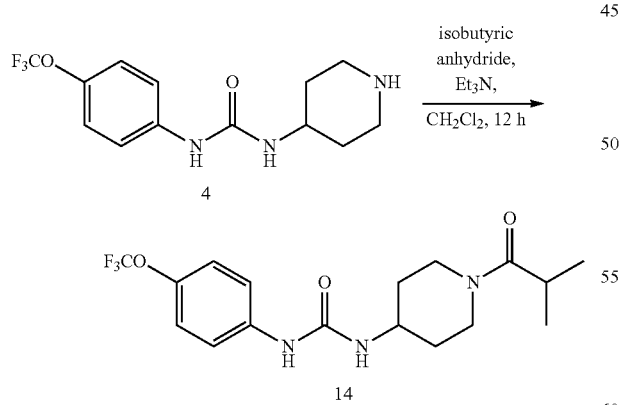

Isobutyric anhydride (40 mg, 253 mmol) was added to a suspension of 4 (80 mg, 264 mmol) in a solution of Et$_3$N (28 mg, 278 mmol) in CH$_2$Cl$_2$ (100 mL). The reaction was stirred at rt for 12 h. The reaction was quenched with HCl solution (2 M). The organic layer was collected and the aqueous layer was further extracted with EtOAc three times. The combined organic layer was dried over anh. MgSO$_4$ and further concentrated under vacuo. The product was purified by flash chromatography (EtOAc:Hex/9:1) and was further purified by recrystallization with MeOH/H$_2$O yielding the final product (96 mg, 257 mmol, % yield). H-NMR (DMSO-$d_6$) ∂ 0.99 (d, J=3 Hz, 6H), 1.26 (m, 2H), 1.84 (t, J=12 Hz, 2H), 2.77 (t, J=12 Hz, 1H), 2.87 (m, 1H), 3.16 (t, J=12 Hz, 1H), 3.71 (m, 1H), 3.84 (d, J=12 Hz, 1H), 4.20 (d, J=12 Hz, 1H), 6.24 (d, J=7.5 Hz, 1H), 7.22 (d, J=9 Hz, 2H), 7.47 (d, J=9 Hz, 2H), 8.56 (s, 1H). F-NMR (DMSO-$d_6$) ∂ −57.17. HRMS (calculated for [H$^+$]: $C_{17}H_{22}F_3N_3O_3$): 374.1692. found (ESI(+), [M-H$^+$]): 374.1665. Melting point: 179.1-180.3 (179.6).

Example 14

Synthesis of tert-butyl (1-(2-methylbutanoyl)piperidin-4-yl)carbamate (15)

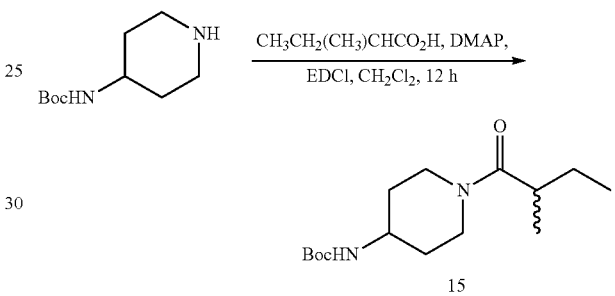

tert-butyl piperidin-4-ylcarbamate (1 g, 5 mmol), 4-(N,N-dimethylamino)piperidine (0.73 g, 6 mmol) and EDCl (1.15 g, 6 mmol) were added into a solution of 2-methylbutanoic acid (0.612 g, 6 mmol) in CH$_2$Cl$_2$ (200 mL). The reaction was stirred overnight at rt. The reaction was quenched with the addition of 0.1 M HCl. The organic layer was further washed with sat. NaHCO$_3$ solution followed by sat. NaCl solution. The organic layers was concentrated under vacuo. The product was purified by flash chromatography (Hex:EtOAc/1:1) yielding final product 15 (1.3 g, 4.6 mmol, 91.5% yield). H-NMR (DMSO-$d_6$) ∂ 0.79 (q, J=5 Hz, 3H), 0.95 (m, 3H), 1.2-1.3 (m, 2H), 1.38 (s, 9H), 1.50 (m, 2H), 1.73 (t, J=15 Hz, 1H), 2.6-2.7 (m, 2H), 3.06 (t, J=12 Hz, 1H), 3.46 (m, 1H), 3.88 (d, J=12 Hz, 1H), 4.26 (m, 1H), 6.85 (d, J=8 Hz, 1H).

Example 15

Synthesis of 1-(4-aminopiperidin-1-yl)-2-methylbutan-1-one (16)

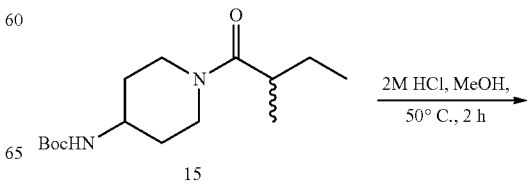

-continued

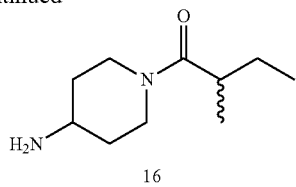
16

Protected piperidine 15 (1.2 g, 4.55 mmol) was dissolved in HCl/MeOH (2 M). The reaction mixture was stirred at 50° C. for 2 h. The crude was concentrated under vacuo and was washed with dichloromethane twice. The crude was basified by NaOH solution (6N) to pH 12. The crude was extracted by EtOAc for 6 times. The combined organic layers was evaporated under vacuo yielding final product 16 (724 mg, 3.93 mmol, 86%). H-NMR (DMSO-$d_6$) ∂ 0.78 (q, J=6 Hz, 3H), 0.95 (t, J=5 Hz, 3H), 1.09 (m, 2H), 1.26 (m, 1H), 1.53 (m, 1H), 1.74 (m, 2H), 2.67 (m, 2H), 2.80 (br, 1H), 3.03 (br, 1H), 3.87 (d, J=12 Hz, 1H), 4.23 (br, 1H).

Example 16

Synthesis of 1-cyclohexyl-3-(1-(2-methylbutanoyl) piperidin-4-yl)urea (17)

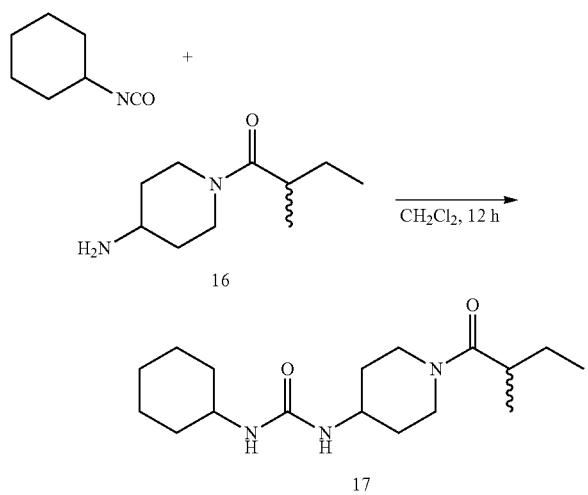

The synthesis of 1-cyclohexyl-3-(1-(2-methylbutanoyl)piperidin-4-yl)urea 17 follows Method 2. Cyclohexyl isocyanate (50 mg, 0.4 mmol) was added to a suspension of 14 (88 mg, 0.5 mmol) in $CH_2Cl_2$ (100 mL). The reaction was stirred overnight at rt. The reaction was quenched with the addition of HCl solution (2 M, 50 mL). The organic layer was collected and the aqueous layer was further extracted with EtOAc three times. The combined organic layers was washed with sat. NaCl solution. The organic layer was concentrated under vacuo. The product was purified by flash chromatography (EtOAc) yielding final product (80 mg, 0.259 mmol, 65% yield). H-NMR (DMSO-$d_6$) ∂ 0.79 (m, 3H), 0.95 (m, 3H), 1.07 (m, 4H), 1.23 (m, 5H), 1.52 (m, 2H), 1.61 (m, 2H), 1.72 (m, 4H), 2.70 (m, 1H), 2.75 (m, 1H), 3.11 (t, J=12 Hz, 1H), 3.34 (m, 1H), 3.58 (m, 1H), 3.83 (d, J=12 Hz, 1H), 4.17 (br, 1H), 5.60 (t, J=8 Hz, 1H), 5.73 (m, 1H). C-NMR (DMSO-$d_6$) ∂ 11.74, 17.38, 24.5, 25.31, 26.71, 33.31, 33.44, 35.66, 43.67, 46.16, 47.60, 156.58, 173.53. HRMS (calculated for [$H^+$]: $C_{17}H_{31}N_3O_2$): 310.2495. found (ESI(+), [M-$H^+$]): 310.2490. Melting point: 127.7-130.5 (128.5).

Example 17

Synthesis of 1-cycloheptyl-3-(1-(2-methylbutanoyl) piperidin-4-yl)urea (18)

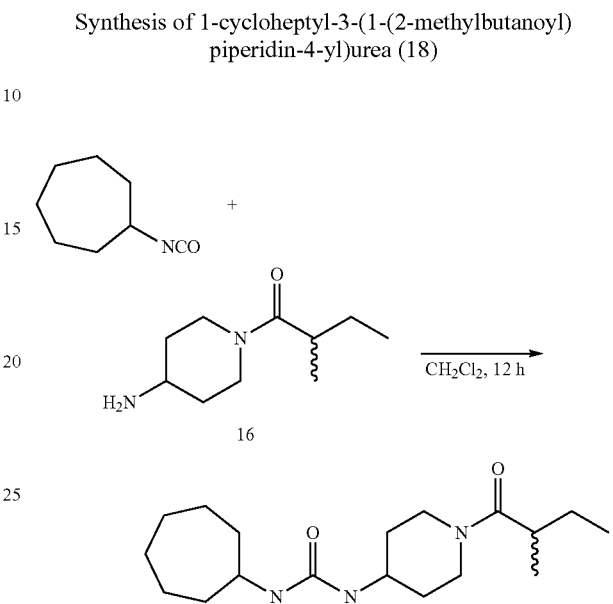

The synthesis of 18 follows Method 2. Cycloheptyl isocyanate (50 mg, 360 mmol) was used and the product was purified by flash chromatography using (EtOAc:Hex/9:1) yielding the final product (93 mg, 0.288 mmol, 80% yield). H-NMR (DMSO-$d_6$) ∂ 0.79 (t, J=6 Hz, 3H), 0.95 (m, 3H), 1.14 (m, 3H), 1.33 (m, 4H), 1.50 (m, 7H), 1.70 (m, 4H), 2.68 (m, 1H), 2.76 (m, 1H), 3.11 (t, J=12 Hz, 1H), 3.56 (m, 1H), 3.82 (d, J=12 Hz, 1H), 4.16 (br, 1H), 5.62 (tbr, 1H), 5.70 (d, 1=6 Hz, 1H). HRMS (calculated for [$H^+$]: $C_{18}H_{33}N_3O_2$): 324.2651. found (ESI(+), [M-$H^+$]): 324.2623. Melting point: 122.4-124.2 (122.9).

Example 18

Synthesis of 1-(4-isopropylphenyl)-3-(1-(2-methylbutanoyl)piperidin-4-yl)urea (19)

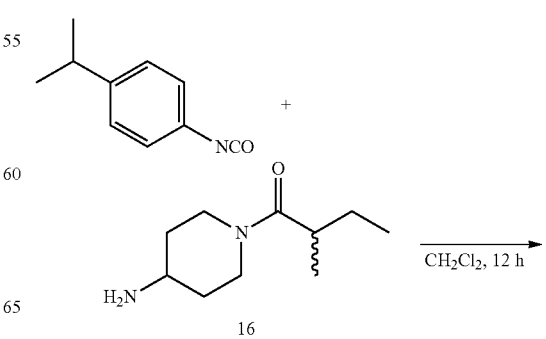

-continued

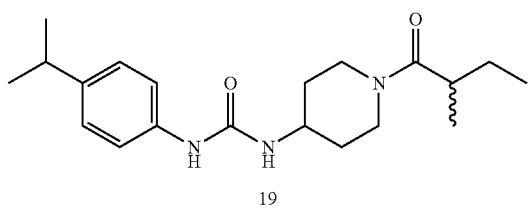

19

The synthesis of 19 follows Method 2. 4-Isopropylphenyl isocyanate (50 mg, 0.311 mmol) was used and the product was purified by flash chromatography using (EtOAc:Hex/8:2) yielding the final product (100 mg, 289 mmol, 93% yield). H-NMR (DMSO-$d_6$) ∂ 0.80 (q, J=6 Hz, 3H), 0.97 (t, J=6 Hz, 3H), 1.15 (d, J=6 Hz, 6H), 1.26 (m, 2H), 1.54 (m, 1H), 1.83 (m, 1H), 2.71 (m, 1H), 2.78 (m, 1H), 3.16 (t, J=9 Hz, 1H), 3.69 (m, 1H), 3.87 (d, J=9 Hz, 1H), 4.20 (br, 1H), 6.13 (t, J=6 Hz, 1H), 7.07 (d, J=6 Hz, 2H), 7.26 (d, 1=6 Hz, 2H), 8.20 (d, J=9 Hz, 1H). HRMS (calculated for [H$^+$]: $C_{20}H_{31}F_3N_3O_2$): 346.2495. found (ESI(+), [M-H$^+$]): 345.2462. Melting point: 174.0-174.9 (174.5).

Example 19

Synthesis of 1-(3,5-di-trifluoromethylphenyl)-3-(1-(2-methylbutanoyl)piperidin-4-yl)urea (20)

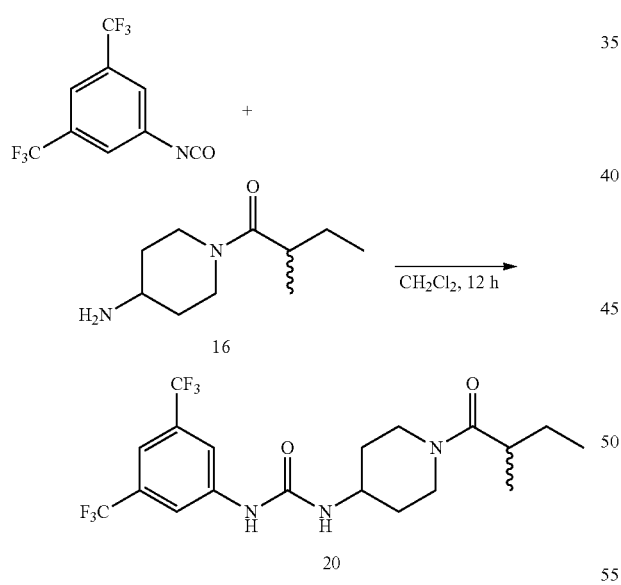

20

The synthesis of 20 follows Method 2. 3,5-di(trifluoromethyl)phenyl isocyanate (50 mg, 196 mmol) was used and the product was purified by flash chromatography using (EtOAc:Hex/7:3) and further purified by recrystallization using methanol and water yielding the final product (78 mg, 177 mmol, 90% yield). H-NMR (DMSO-$d_6$) ∂ 0.80 (q, J=6 Hz, 3H), 0.97 (t, J=6 Hz, 3H), 1.27 (m, 2H), 1.53 (m, 1H), 1.85 (br, 1H), 2.72 (m, 2H), 3.14 (t, J=12 Hz, 1H), 3.73 (m, 1H), 3.90 (d, J=12 Hz, 1H), 4.28 (br, 1H), 6.56 (t, J=6 Hz, 1H), 7.54 (s, 1H), 8.07 (s, 2H), 9.19 (d, J=9 Hz, 1H). F-NMR (DMSO-$d_6$) ∂ −61.75. HRMS (calculated for [H$^+$]: $C_{19}H_{23}F_6N_3O_2$): 440.1773. found (ESI(+), [M-H$^+$]): 440.1761. Melting point: 211.0-213.5 (212.0)

Example 20

Synthesis of 1-(4-tert-butylphenyl)-3-(1-(2-methylbutanoyl)piperidin-4-yl)urea (21)

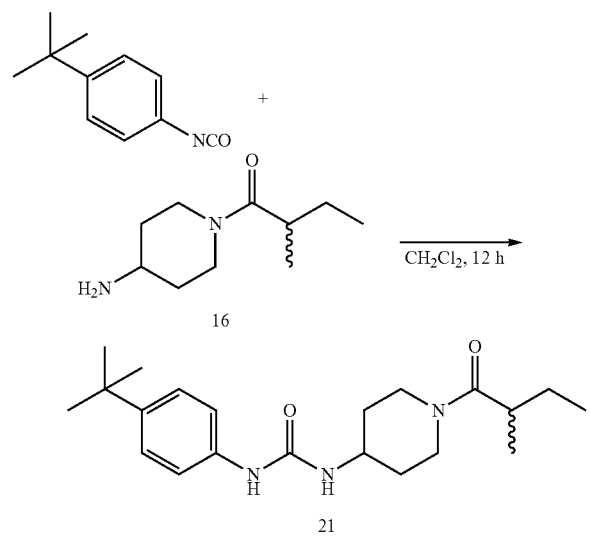

21

The synthesis of 20 follows Method 2. 4-(t-butyl)phenyl isocyanate (50 mg, 139 mmol) was used and the product was purified by flash chromatography using (EtOAc:Hex/) and further purified by recrystallization using methanol and water yielding the final product (86 mg, 240 mmol, 84% yield). H-NMR (DMSO-$d_6$) ∂ 0.78 (q, J=6 Hz, 3H), 0.97 (t, J=6 Hz, 3H), 1.24 (m, 11H), 2.71 (m, 2H), 3.19 (t, J=12 Hz, 1H), 3.65 (m, 1H), 3.90 (d, J=12 Hz, 1H), 4.28 (br, 1H), 6.56 (t, J=6 Hz, 1H), 7.54 (s, 1H), 8.07 (s, 2H), 9.19 (d, J=9 Hz, 1H). HRMS (calculated for [H$^+$]: $C_{21}H_{33}N_3O_2$): 360.2651. found (ESI(+), [M-H$^+$]): 360.2621. Melting point: 213.2-216.6 (214.3).

Example 21

Synthesis of 1-(1-(2-methylbutanoyl)piperidin-4-yl)-3-(4-(trifluoromethoxy)phenyl)urea

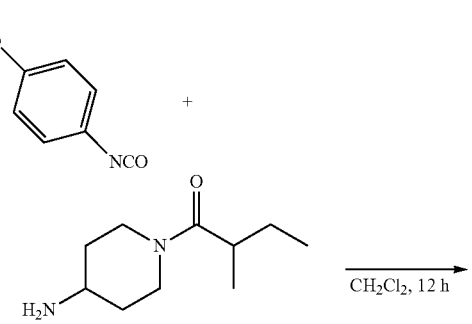

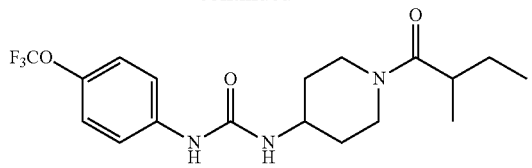

4-(Trifluoromethoxy)phenylisocyanate (100 mg, 0.49 mmol) and 1-(4-aminopiperidin-1-yl)-2-methylbutan-1-one (90 mg, 0.49 mmol) was dissolved in CH₂Cl₂ (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography (EtOAc:Hex/1:1) yielding final product (168 mg, 4.39 mmol, 89%). H-NMR (DMSO-d₆) δ 0.80 (m, 3H), 0.97 (m, 3H), 1.28 (m, 3H), 1.53 (m, 1H), 1.85 (tbr, 2H), 2.71 (m, 1H), 2.78 (m, 1H), 3.16 (t, J=12 Hz, 1H), 3.71 (m, 1H), 3.88 (d, J=12 Hz, 1H), 4.21 (br, 1H), 6.26 (tbr, 1H), 7.22 (d, J=9 Hz, 2H), 7.47 (d, J=9 Hz, 2H), 8.55 (d, J=9 Hz, 2H).

Example 22

Synthesis of 1-(4-ethylcyclohexyl)-3-(1-isobutyrylpiperidin-4-yl)urea

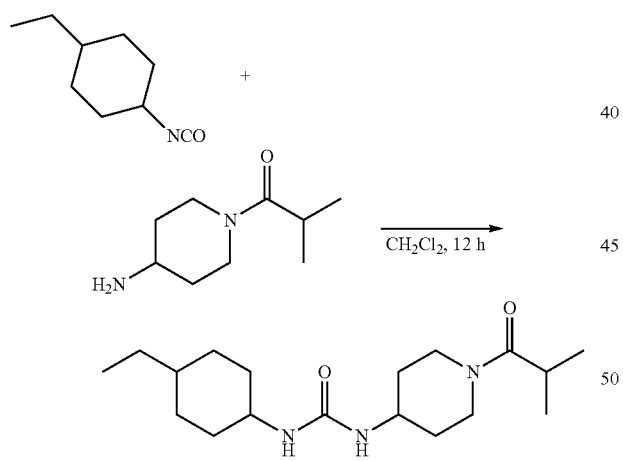

4-(Trifluoromethyl)phenylisocyanate (100 mg, 0.65 mmol) and 1-(4-aminopiperidin-1-yl)-2-methylbutan-1-one (111 mg, 0.53 mmol) was dissolved in CH₂Cl₂ (100 mL) and stirred for 12 h. The reaction was quenched by addition of water. The organic layer was isolated and the aqueous layer was extracted with EtOAc for 4 times. The combined organic layer was concentrated under vacuo and was further purified by flash chromatography (EtOAc:Hex/1:1) yielding final product (89 mg, 2.76 mmol, 42%). H-NMR (DMSO-d₆) δ 0.83 (t, J=8 Hz, 3H), 0.91 (m, 1H), 0.97 (m, 7H), 1.03 (m, 3H), 1.16 (m, 4H), 1.69 (m, 3H), 1.78 (m, 3H), 2.72 (t, J=12 Hz, 1H), 2.85 (m, 1H), 3.10 (t, J=12 Hz, 1H), 3.24 (m, 1H), 3.57 (m, 1H), 3.79 (d, J=13 Hz, 1H), 4.14 (d, J=13 Hz, 1H), 5.56 (d, J=7.5 Hz, 1H), 5.70 (d, J=7.5 Hz, 1H).

Example 23

1-(1-(2-ethylbutanoyl)piperidin-4-yl)-3-(4-(trifluoromethoxy)phenyl)urea

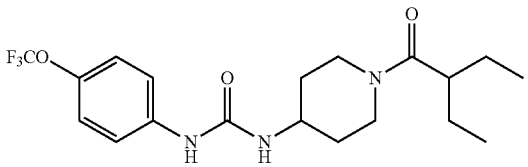 [SMILES: CCC(CC)C(=O)N1CCC(NC(=O)Nc2ccc(OC(F)(F)F)cc2)CC1]

To an ice cold solution of 4-(trifluoromethoxy)phenyl isocyanate (60.9 mg, 0.3 mmol) in THF (1.5 ml) was added 1-(4-aminopiperidin-1-yl)-2-ethylbutan-1-one (59.4 mg, 0.3 mmol), prepared via Example 14 and Example 15 using 2-ethylbutanoic acid. The reaction mixture was allowed to warm to rt and stirred overnight. 1 M HCl aqueous solution was added followed by extraction with EtOAc. Flash chromatography eluted with 50:1 DCM:MeOH followed by recrystallization from acetone afforded desired compound (65 mg, 54%) as a white solid. Mp 167.0-167.4° C. ¹H NMR (600 MHz, DMSO-d₆) δ 8.50 (s, 1H), 7.47 (d, J=9.0 Hz, 2H), 7.22 (d, J=8.4 Hz, 2H), 6.28 (d, J=7.8 Hz, 1H), 4.27 (brd, J=13.2 Hz, 1H), 3.95 (brd, J=15.6 Hz, 1H), 3.75-3.69 (m, 1H), 3.18 (t, J=11.1 Hz, 1H), 2.81 (t, J=10.8 Hz, 1H), 2.68-2.60 (m, 1H), 1.88 (d, J=10.8 Hz, 1H), 1.82 (d, J=10.8 Hz, 1H), 1.51-1.45 (m, 2H), 1.45-1.30 (m, 2H), 1.30-1.10 (m, 2H), 0.83-0.75 (m, 6H). F NMR (300 MHz, DMSO-d6) −57.545 (s).

Example 24

1-(1-(2-ethylbutanoyl)piperidin-4-yl)-3-(4-(trifluoromethyl)phenyl)urea

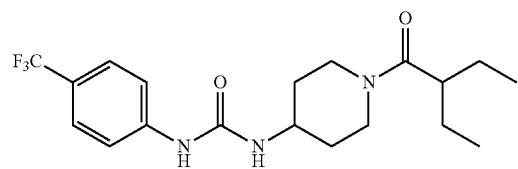 [SMILES: CCC(CC)C(=O)N1CCC(NC(=O)Nc2ccc(C(F)(F)F)cc2)CC1]

To an ice cold solution of 4-(trifluoromethyl)phenyl isocyanate (56.1 mg, 0.3 mmol) in THF (1.5 ml) was added 1-(4-aminopiperidin-1-yl)-2-ethylbutan-1-one (59.4 mg, 0.3 mmol), prepared via Example 14 and Example 15 using 2-ethylbutanoic acid. The reaction mixture was allowed to warm to rt and stirred overnight. 1 M HCl aqueous solution was added followed by extraction with EtOAc. Flash chromatography eluted with 50:1 DCM:MeOH followed by recrystallization from acetone afforded desired compound (64 mg, 55%) as a white solid. Mp 207.9-209.3° C. ¹H NMR (400 MHz, DMSO-d₆) δ 8.74 (s, 1H), 7.57 (m, 4H), 6.40 (d, J=7.6 Hz, 1H), 4.28 (brd, J=12.4 Hz, 1H), 3.96 (brd, J=13.6 Hz, 1H), 3.78-3.70 (m, 1H), 3.18 (t, J=11.6 Hz, 1H), 2.82 (t, J=11.0 Hz, 1H), 2.67-2.60 (m, 1H), 1.89 (d, J=10.8 Hz, p 1H), 1.83 (d, J=10.4 Hz, 1H), 1.56-1.42 (m, 2H), 1.42-1.31 (m, 2H), 1.31-1.16 (m, 2H), 0.83-0.75 (m, 6H). F NMR (300 MHz, DMSO-d6) −60.324 (s).

Example 25

Pharmacokinetic Study

Enzyme Purification.

Recombinant murine and human sEH were produced in a polyhedron positive baculovirus expression system, and were purified by affinity chromatography as previously reported (*Arch. Biochem. Biophys.* 1993, 305, 197-201; *J. Biol. Chem.* 1993, 268, 17628-17633; *Anal. Biochem.* 1988, 169, 71-80).

$IC_{50}$ Assay Conditions.

$IC_{50}$ values were determined using a sensitive fluorescent based assay (*Anal. Biochem.* 2005, 343, 66-75). Cyano(2-methoxynaphthalen-6-yl)methyl trans-(3-phenyl-oxyran-2-yl) methyl carbonate (CMNPC) was used as the fluorescent substrate. Human sEH (1 nM) or murine sEH (1 nM) was incubated with the inhibitor for 5 min in pH 7.0 Bis-Tris/HCl buffer (25 mM) containing 0.1 mg/mL of BSA at 30° C. prior to substrate introduction ([S]=5 µM). Activity was determined by monitoring the appearance of 6-methoxy-2-naphthaldehyde over 10 minutes by fluorescence detection with an excitation wavelength of 330 nm and an emission wavelength of 465 nm. Reported $IC_{50}$ values are the average of three replicates. The fluorescent assay as performed here has a standard error between 10 and 20%, suggesting that differences of two-fold or greater are significant (*Anal. Biochem.* 2005, 343, 66-75).

Pharmacokinetics (PK) Study.

Male CFW mice (7 week old, 24-30 g) were purchased from Charles River Laboratories. All the experiments were performed according to protocols approved by the Animal Use and Care Committee of University of California, Davis. Inhibitors (1 mg each) were dissolved in 1 mL of oleic acid-rich triglyceride containing 20% polyethylene glycol (average molecular weight: 400) to give a clear solution for oral administration. Each compound was orally administered to 3 or 4 mice at a dose of 5 mg/kg in 120-150 µl of vehicle depending on animal weight. Blood (10 µL) was collected from the tail vein using a pipette tip rinsed with 7.5% EDTA (K3) at 0, 0.5, 1, 1.5, 2, 4, 6, 8, 24 hours after oral dosing with the inhibitor. The blood samples were prepared according to the methods detailed in our previous study (*Br. J. Pharmacol.* 2009, 156, 284-296). Blood samples were analyzed using an Agilent 1200 Series HPLC equipped with a 4.6 mm×150 mm Inertsil ODS-4 3 µm column (GL Science Inc., Japan) held at 40° C. and coupled with an Applied Biosystems 4000 QTRAP hybrid, triple-quadrupole mass spectrometer. The instrument was equipped with a linear ion trap and a Turbo V ion source and was operated in positive ion MRM mode (see Table 6). The solvent system consisted of water/acetic acid (999/1 v/v, solvent A) and acetonitrile/acetic acid (999/1 v/v; solvent B). The gradient was begun at 30% solvent B and was linearly increased to 100% solvent B in 5 min. This was maintained for 3 min, then returned to 30% solvent B in 2 min. The flow rate was 0.4 mL/min. The injection volume was 10 µL and the samples were kept at 4° C. in the auto sampler.

There is less than 5% variation in compound levels in replicate blood samples from the same mice. Thus the standard deviation shown in Figure S2 represents variation among mice treated with the same compound. The PK parameters of individual mice were calculated by fitting the time dependent curve of blood inhibitor concentration (Figure S2) to a non-compartmental analysis with the WinNonlin software (Pharsight, Mountain View, Calif.). Parameters determined include the time of maximum concentration ($T_{max}$), maximum concentration ($C_{max}$), half-life ($t_{1/2}$), and area under the concentration-time curve to terminal time (AUC). In separate studies to determine dose linearity of selected compounds, pharmacokinetic parameters determined by cassette dosing were found to be predictive of results from dosing individual compounds (*Br. J Pharmacol.* 2009, 156, 284-296; *Anal. Chico. Acta.* 2006, 559, 37-44).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of 1-(1-(2-methylbutyryl)piperidin-4-yl)-3-(4-(trifluoromethoxy)phenyl)urea, (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, 1-(1-(2-ethylbutanoyl)piperidin-4-yl)-3-(4-(trifluoromethoxy)phenyl)urea, 1-(1-(2-ethylbutanoyl)piperidin-4-yl)-3-(4-(trifluoromethyl)phenyl)urea, (S)-1-(1-(2-methylbutanoyl)piperidin-4-yl)-3-(4-(trifluoromethyl)phenyl)urea, 1-cyclohexyl-3-(1-(2-methylbutanoyl)piperidin-4-yl)urea, 1-cycloheptyl-3-(1-(2-methylbutanoyl)piperidin-4-yl)urea, 1-(4-isopropylphenyl)-3-(1-(2-methyl butanoyl)piperidin-4-yl)urea, 1-(3,5-di-trifluoromethylphenyl)-3-(1-(2-methylbutanoyl)piperidin-4-yl)urea, 1-(4-tert-butylphenyl)-3-(1-(2-methyl butanoyl)piperidin-4-yl)urea, 1-(4-ethylcyclohexyl)-3-(1-isobutyrylpiperidin-4-yl)urea, or salts thereof.

2. The compound of claim 1, selected from the group consisting of 1-(1-(2-methylbutyryl)piperidin-4-yl)-3-(4-(trifluoromethoxy)phenyl)urea, (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, and (S)-1-(1-(2-methylbutanoyl)piperidin-4-yl)-3-(4-(trifluoromethoxy)phenyl)urea.

3. The compound of claim 1, selected from the group consisting of (S)-1-(1-(2-methylbutanoyl)piperidin-4-yl)-3-(4-(trifluoromethyl)phenyl)urea, 1-(1-isobutyrylpiperidin-4-yl)-3-(4-(trifluoromethoxy)phenyl)urea, and (S)-1-(1-(2-methyl butanoyl)piperidin-4-yl)-3-(4-(trifluoromethoxy)phenyl)urea.

4. The compound of claim 1, wherein the compound is (S)-1-(1-(2-methylbutanoyl)piperidin-4-yl)-3-(4-(trifluoromethyl)phenyl)urea.

5. The compound of claim 1, wherein the compound is 1-(1-isobutyrylpiperidin-4-yl)-3-(4-(trifluoromethoxy)phenyl)urea.

6. The compound of claim 1, wherein the compound is (S)-1-(1-(2-methylbutanoyl)piperidin-4-yl)-3-(4-(trifluoromethoxy)phenyl)urea.

7. A pharmaceutical composition comprising a compound of claim 1 and a pharmaceutical excipient.

8. A method for inhibiting a soluble epoxide hydrolase, the method comprising contacting the soluble epoxide hydrolase with a therapeutically effective amount of a compound of claim 1, thereby inhibiting the soluble epoxide hydrolase.

9. A method for monitoring the activity of a soluble epoxide hydrolase, the method comprising contacting the soluble epoxide hydrolase with an amount of a compound of claim 1 sufficient to produce a detectable change in the fluorescence of the soluble epoxide hydrolase by interacting with one or more tryptophan residues present in the catalytic site of said soluble epoxide hydrolase, thereby monitoring the activity of the soluble epoxide hydrolase.

* * * * *